US008778888B2

(12) United States Patent
Cochran et al.

(10) Patent No.: US 8,778,888 B2
(45) **Date of Patent: *Jul. 15, 2014**

(54) CYSTINE KNOT PEPTIDES BINDING TO ALPHA IIB BETA 3 INTEGRINS AND METHODS OF USE

(75) Inventors: Jennifer R. Cochran, Stanford, CA (US); Adam P. Silverman, Redwood City, CA (US); Mihalis S. Kariolis, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 12/938,216

(22) Filed: Nov. 2, 2010

(65) Prior Publication Data

US 2011/0136740 A1 Jun. 9, 2011

Related U.S. Application Data

(60) Provisional application No. 61/272,816, filed on Nov. 6, 2009.

(51) Int. Cl.

| | |
|---|---|
| ***C07K 14/00*** | (2006.01) |
| ***A61K 38/16*** | (2006.01) |
| ***A61K 38/36*** | (2006.01) |

(52) U.S. Cl.

USPC .......................... 514/21.3; 514/13.8; 530/325

(58) Field of Classification Search

None

See application file for complete search history.

(56) References Cited

U.S. PATENT DOCUMENTS

| | | | |
|---|---|---|---|
| 4,789,734 | A | 12/1988 | Pierschbacher |
| 4,792,525 | A | 12/1988 | Ruoslahti et al. |
| 4,879,237 | A | 11/1989 | Rudslahti et al. |
| 4,988,621 | A | 1/1991 | Ruoslahti et al. |
| 5,169,930 | A | 12/1992 | Ruoslahti et al. |
| 5,519,005 | A | 5/1996 | Lider et al. |
| 5,536,814 | A | 7/1996 | Ruoslahti et al. |
| 5,695,997 | A | 12/1997 | Ruoslahti et al. |
| 5,766,591 | A | 6/1998 | Brooks et al. |
| 5,827,821 | A | 10/1998 | Pierschbacher et al. |
| 5,880,092 | A | 3/1999 | Pierschbacher et al. |
| 5,916,875 | A | 6/1999 | Ruoslahti et al. |
| 5,981,468 | A | 11/1999 | Pierschbacher et al. |
| 5,981,478 | A | 11/1999 | Ruoslahti et al. |
| 5,994,501 | A | 11/1999 | Ruoslahti et al. |
| 6,020,460 | A | 2/2000 | Pierschbacher et al. |
| 6,180,610 | B1 | 1/2001 | Ruoslahti et al. |
| 6,265,539 | B1 | 7/2001 | Arlinghaus |
| 6,353,090 | B1 | 3/2002 | Pierschbacher et al. |
| 6,451,976 | B1 | 9/2002 | Lu et al. |
| 6,962,974 | B1 | 11/2005 | Kalluri |
| 2002/0018780 | A1 | 2/2002 | Koenig et al. |
| 2004/0132659 | A1 | 7/2004 | Markland, Jr. et al. |
| 2004/0146976 | A1 | 7/2004 | Wittrup et al. |
| 2005/0075323 | A1 | 4/2005 | Day et al. |
| 2005/0164300 | A1 | 7/2005 | Artis et al. |
| 2005/0196427 | A1 | 9/2005 | Tirrell et al. |
| 2006/0029544 | A1 | 2/2006 | Sutcliffe-Goulden et al. |
| 2009/0257952 | A1 * | 10/2009 | Cochran et al. .............. 424/1.69 |

FOREIGN PATENT DOCUMENTS

| | | | |
|---|---|---|---|
| WO | 2008045252 | A2 | 4/2008 |

OTHER PUBLICATIONS

Kuwada, 1994, Peptide Chemistry, p. 29-32.*
Yu, 1993, Biochemistry, 32, p. 13123-13129.*
Heck, 1994, JACS, 116, 10426-10436.*
Bures, 1998, Biochemistry, 37, p. 12172-12177.*
Ana Segura, et al., "Snakin-1, a peptide from potato that is active against plant pathogens," MPMI, 1999, vol. 12, 16-23.
Jean-Christophe Gelly, et al., "The KNOTTIN website and database: a new information system dedicated to the knottin scaffold," Nucleic Acids Research, 2004, vol. 32, D156-D159.
Andreas Christmann, et al., "The cystine knot of a squash-type protease inhibitor as a structural scaffold for *Escherichia coli* cell surface display of conformationally constrained peptides," Protein Engineering, 1999, vol. 12, 797-806.
FlowJo, Data analysis software for flow cytometry, User Documentation tutorial, Version 3.4, Apr. 2001.
Joseph C. McNulty, et al., "High-resolution NMR structure of the chemically-synthesized melanocortin receptor binding domain AGRP(87-132) of the agouti-related protein," Biochemistry, 2001, vol. 40, 15520-15527.
Valerie Copie, et al., "Solution structure and dynamics of linked cell attachment modules of mouse fibronectin containing the RGD and synergy regions: comparison with the human fibronectin crystal structure," J. Mol. Biol., 1998, vol. 277, 663-682.
Norelle L. Daly, et al., "Disulfide folding pathways of cystine knot proteins," J. Biol. Chem., 2003, vol. 278, 6314-6322.
Aarno Hautanen, et al., "Effects of modifications of the RGD sequence and its context on recognition by the fibronectin receptor," J. Biol. Chem., 1989, vol. 264, 1437-1442.
C. S. Elangbam, et al., "Cell adhesion molecules—update," Vet Pathol, 1997, 34,61-73.
Leonore A. Herzenberg, et al., "Intepreting flow cytometry data: a guide for the perplexed," Nature Immunology, 2006, vol. 7, 681-685.
Shuang Liu, "Radiolabeled multimeric cyclic RGD peptides as integrin $\alpha v\beta 3$ targeted radiotracers for tumor imaging," Molecular Pharmaceutics, 2006, vol. 3, 472-487.

(Continued)

*Primary Examiner* — Satyanarayana R Gudibande

(74) *Attorney, Agent, or Firm* — David J. Aston; Peters Verny, LLP

(57) ABSTRACT

Disclosed are peptides having a cystine knot structural motif and comprising a sequence engineered for specificity against $\alpha_{IIb}\beta_3$ integrin, found on platelets, and a method of using the same in anti-thrombotic therapies. The present peptides utilize a cystine knot scaffold derived from modified agouti-related protein or agatoxin, An alternate library screening strategy was used to isolate variants of peptides that selectively bound to $\alpha_{IIb}\beta_3$ integrin or to both $\alpha_{IIb}\beta_3$ and $\alpha_V\beta_3$ integrins. Unique consensus sequences were identified within the identified peptides suggesting alternative molecular recognition events that dictate different integrin binding specificities. In addition, the engineered peptides prevented human platelet aggregation in a plasma-based assay and showed high binding affinity for $\alpha_{IIb}\beta_3$ integrin.

20 Claims, 8 Drawing Sheets

(56) References Cited

OTHER PUBLICATIONS

Arne Skerra, "Engineered protein scaffolds for molecular recognition," J. Mol. Recognition, 2000, vol. 13, 167-187.
Beth Wattam, et al., "Arg-Tyr-Asp (RYD) and Arg-Cys-Asp (RCD) motifs in dendroaspin promote selective inhibition of β1 and β3 integrins," Biochem. J., 2001, vol. 356, 11-17.
Ralf J. Hosse, et al., "A new generation of protein display scaffolds for molecular recognition," Protein Science, 2006, vol. 15, 14-27.
Geoffrey P. Smith, et al., "Small binding proteins selected from a combinatorial repertoire of knottins displayed on phage," J. Mol. Biol., 1998, vol. 277, 317-332.
Robert M. Scarborough, et al., "Characterization of the integrin specificities of disintegrins isolated from american pit viper venoms," J. Biol. Chem., 1993, vol. 268, 1058-1065.
Thomas J. Kunicki, et al., "The exchange of Arg-Gly-Asp (RGD) and Arg-Tyr-Asp (RYD) binding sequences in a recombinant murine Fab fragment specific for the integrin αIIbβ3 does not alter integrin recognition," J. Biol. Chem., 1995, vol. 270, 16660-16665.
Herren Wu, et al., "Stepwise in vitro affinity maturation of vitaxin, an αvβ3-specific humanized mAb," PNAS, 1998, vol. 95, 6037-6042.
Victor M. Garsky, et al., "Chemical synthesis of echistatin, a potent inhibitor of platelet aggregation from *Echis carinatus*: synthesis and biological activity of selected analogs," PNAS, 1989, vol. 86, 4022-4026.
Sandy Reiss, et al., "Inhibition of platelet aggregation by grafting RGD and KGD sequences on the structural scaffold of small disulfide-rich proteins," Platelets, 2006, vol. 17, 153-157.
Richard H. Kimura, et al., "Engineered knottin peptides: A new class of agents for imaging integrin expression in living subjects," Cancer Research, 2009, vol. 69, 2435-2442.
Alexander Wentzel, et al., "Sequence requirements of the GPNG beta-turn of the *Ecballium elaterium* trypsin inhibitor II explored by combinatorial library screening," J. Biol. Chem., 1999, vol. 274, 21037-21043.
Erkki Kolvunen, et al., "Phage libraries displaying cyclic peptides with different ring sizes: ligand specificities of the RGD-directed integrins," Nature Biotechnology, 1995, vol. 13, 265-270.
Peter C. Brooks, et al., "Requirement of vascular integrin αvβ3 for angiogenesis," Science, 1994, vol. 264, 569-571.
A. Favel, et al., "Protease inhibitors from *Ecballium elaterium* seeds," Int. J. Peptide Protein Res., 1989, vol. 33, 202-208.
Timothy Hla, et al., "Human cyclooxygenase-2 cDNA," PNAS, 1992, vol. 89, 7384-7388.
PCT International Search Report for application PCT/US 07/21218 dated May 29, 2008.
Final Office Action for U.S. Appl. No. 12/418,376 dated Jan. 27, 2011.
Adam P. Silverman, et al., Engineered Cystine-Knot Peptides That Bind αvβ3 Integrin With Antibody-Like Affinities, J. Mol. Biol., 2009, vol. 385(4), 1064-1075.

* cited by examiner

GCVRLHESCLGQQVPCCDPAATCYCRFFNAFCYCR

(SEQ ID No: 3)

CYSTINE KNOT PEPTIDES BINDING TO ALPHA IIB BETA 3 INTEGRINS AND METHODS OF USE

FEDERALLY-SPONSORED RESEARCH OR DEVELOPMENT

This invention was made with Government support under Contract PHS NRSA 5T32 CA09302 awarded by the National Institutes of Health. The Government has certain rights in this invention.

CROSS-REFERENCE TO RELATED APPLICATIONS

This application claims priority from U.S. Provisional Patent Application No. 61/272,816, filed Nov. 6, 2009, which is hereby incorporated by reference in its entirety.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file. Applicants incorporate the contents of the sequence listing by reference in its entirety.

BACKGROUND OF THE INVENTION

1. Field of the Invention

The present invention relates to the field of engineered peptides, and to the field of peptides which bind to integrins, and particularly to integrin binding peptides that bind to platelet integrins and methods of using the peptides in anti-thrombotic therapies.

2. Related Art

Development of highly specific protein ligands that selectively target a single member in a family of closely related receptors has long been a significant molecular engineering problem. Integrin receptors present a particular challenge because recognition of many family members is mediated by an Arg-Gly-Asp (RGD) consensus sequence. Integrins are a class of diverse heterodimeric (α/β) receptors that are involved in cell adhesion to the extracellular matrix and mediate signaling pathways involved in cell cycle progression. As a result, several family members have generated much interest as potential therapeutic targets in the biomedical and pharmaceutical arenas. Integrins $\alpha_{IIb}\beta_3$ and $\alpha_v\beta_3$ are important clinical targets for prevention of platelet-mediated thrombosis and tumor angiogenesis, respectively; however, the high degree of similarity between these two receptors, as well as the $\alpha_v\beta_5$ integrin, has made it challenging to generate RGD-containing protein ligands that selectively target only a single integrin with high affinity.

An emerging approach for developing novel protein ligands is to use a naturally-occurring protein as a framework, or scaffold, and introducing amino acid mutations that confer recognition to a specific molecular target. Directed evolution is a powerful combinatorial technique for engineering new molecular recognition properties into protein scaffolds, often with remarkable affinities and specificities. By replacing loops or domains with random or rationally designed mutations that sample a large diversity of amino acid sequence space and isolating variants that possess desired molecular recognition properties, new proteins have been generated that bind diverse targets. Ideal protein scaffolds provide a stable, well-structured core and solvent-exposed loops or domains that are highly tolerant to substitution. Protein scaffolds that have been successfully evolved to bind new targets include fibronectin, A-domains, anticalins, ankyrin repeats, and cystine knots, among others.

Cystine knot (knottin) scaffolds have been used previously in other applications that require rapid biodistribution and short in vivo half lives, such as imaging in living subjects, and offer promise as oral peptide drugs. Knottins are a diverse class of small, highly structured polypeptides with up to 60 amino acids in length and possessing a core domain of three or more interwoven disulfide bonds. The structural rigidity conferred by the disulfide-bonded knottin framework leads to exceptionally high thermal and proteolytic stability, and the solvent-exposed loops spanned by these disulfide bonds are moderately to highly tolerant of mutations. Much of the development of knottin as protein-engineering scaffolds have focused on two family members: the *Ecballium elaterium* trypsin inhibitor II (EETI-II) and the melanocortin receptor binding domain of the human Agouti-related protein (AgRP). EETI-II contains three disulfide bonds, while AgRP contains five; therefore several truncated versions of AgRP have been developed to simplify the scaffold. In one study, EETI-II and AgRP have been used as scaffolds to introduce entire grafted loops derived from snake venom disintegrins that contain RGD or KGD integrin-recognition sequences resulting in knottin peptides that inhibit $\alpha_{IIb}\beta_3$, integrin-mediated platelet aggregation with half-maximal inhibitory concentration ($IC_{50}$) values in the micromolar range. This study demonstrated that the structural confirmation of the scaffold and residues flanking the RGD sequence are critically important for the biological activity of the engineered peptides and also suggested that judicious selection of these neighboring residues might be an effective strategy by which to generate knottin peptides with enhanced potency.

Previously, EETI-II and AgRP knottins that bind to integrin $\alpha_v\beta_3$ (the vitronectin receptor) with low- to sub-nanomolar affinities were engineered. In both of these prior studies, peptide mutants that bound $\alpha_v\beta_3$ integrin were identified from yeast-displayed libraries where a single knottin loop was substituted with a loop containing an RGD motif, and randomized flanking residues. Surprisingly, although the library screens were performed only against $\alpha_v\beta_3$ integrin, the two engineered scaffolds showed very different integrin specificities. In addition to binding $\alpha_v\beta_3$ integrin with relative affinities of 10-30 nM, the engineered EETI-II peptides also bound with low nanomolar affinity to the related $\alpha_v\beta_5$ integrin. Moreover, one peptide was found to bind with, high affinity to $\alpha_5\beta_1$ integrin (the fibronectin receptor) as well as to $\alpha_v\beta_3$ and $\alpha_v\beta_5$ integrins. None of these engineered EETI-II peptides bound $\alpha_{IIb}\beta_3$ integrin with affinities stronger than the micromolar range. In contrast, the engineered AgRP peptides, bound $\alpha_v\beta_3$ integrin with high affinity ($K_D$~1-10 nM) but did not appreciably bind to $\alpha_v\beta_5$ or $\alpha_5\beta_1$ integrins. Additionally, the AgRP peptides weakly bound $\alpha_{IIb}\beta_3$ integrin ($K_D$ values could not be accurately determined, due to low affinity, but were estimated at greater than several hundred nM). The specificity of the engineered AgRP peptides for $\alpha_v\beta_3$ integrin was intriguing in light of previous challenges in developing protein scaffolds that could selectively target $\alpha_v\beta_3$ integrin with high affinity over $\alpha_v\beta_5$ and $\alpha_{IIb}\beta_3$ integrins. For example, when phage-displayed libraries of tendamistat analogs were screened for variants that bound to $\alpha_v\beta_3$, $\alpha_v\beta_5$, or $\alpha_{IIb}\beta_3$ integrins, most of the proteins selected bound at least two of these integrins. A common feature in these studies and others is that the conformation of the RGD motif is critical in determining both the affinity and specificity of the ligand-integrin interaction. Accordingly, improved integrin binding affinities and specificities have been achieved with cyclic and highly structured peptides relative to linear peptides. Similarly, the residues flanking the RGD motif have a significant role in determining how the recognition sequence is presented to integrin receptors; thus higher affinities and specificities also have often been achieved when the RGD flanking residues were engineered for optimal binding, using combinational methods, as opposed to simple loop grafting of a sequence from a natural RGD-containing ligand.

To further explore the integrin specificities that can be achieved with engineered cystine-knot peptides, and to expand the repertoire of available integrin-targeting molecules, we sought to determine whether a truncated form of AgRP and AgTx (Agatoxin) which have a C-terminal portion removed, could serve as a scaffold for selectively binding integrins other than $\alpha_v\beta_3$. Engineered AgRP peptides that selectively bind $\alpha_{IIb}\beta_3$ integrin with high affinity versus $\alpha_{IIb}\beta_3$ could also provide insights into the mode of binding between integrins and conformationally-restricted scaffold loops. Moreover, such peptides would have therapeutic potential as $\alpha_{IIb}\beta_3$ integrin plays a critical role in the aggregation of platelets and is a clinically validated target for thrombosis. Despite the successes of three FDA-approved anti-$\alpha_{IIb}\beta_3$ drugs for precautionary or responsive treatment to ischemic complications, there remains an interest in improved $\alpha_{IIb}\beta_3$ integrin inhibitors to prevent platelet-aggregation.

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

SPECIFIC PATENTS AND PUBLICATIONS

US 2009/0257952 by Cochran et al., published Oct. 15, 2009, entitled "Engineered Integrin Binding Peptides," Engineered peptides that bind with high affinity (low equilibrium dissociation constant (Kd)) to the cell surface receptors of fibronectin ($\alpha_5\beta_1$) or vitronectin ($\alpha_v\beta_3$ and $\alpha_v\beta_5$ integrins) are disclosed. The molecular scaffold is preferably based on a knottin, e.g., EETI (Trypsin inhibitor 2 (Trypsin inhibitor II) (EETI-II) [*Ecballium elaterium* (Jumping cucumber)], AgRP (Agouti-related protein), and Agatoxin IVB, which peptides have a rigidly defined three-dimensional conformation.

Silverman et al., "Engineered cystine-knot peptides that bind $\alpha_v\beta_3$ integrin with antibody-like affinities," J Mol Biol. 2009 Jan. 30; 385(4):1064-75. Epub 2008 Nov. 12, discloses a truncated form of the Agouti-related protein (AgRP), a 4 kDa cystine-knot peptide with four disulfide bonds and four solvent-exposed loops, as a scaffold for engineering peptides that bound to $\alpha_v\beta_3$ integrins with high affinity and specificity.

Kimura et al., "Engineered cystine knot peptides that bind $\alpha_v\beta_3$, $\alpha_v\beta_5$, and $\alpha_5\beta_1$ integrins with low-nanomolar affinity," Proteins. 2009 Nov. 1; 77(2):359-69, discloses engineered *Ecballium elaterium* trypsin inhibitor (EETI-II), that to bind to $\alpha_v\beta_3/\alpha_v\beta_5$ or $\alpha_v\beta_3/\alpha_v\beta_5/\alpha_5\beta_1$ integrins.

Varga-Szabo et al., "Cell Adhesion Mechanisms in Platelets," Arterioscler Thromb Vasc Biol. 2008:28:403-412 (March 2008) discloses that platelets express 3 different $\beta_1$-integrins, namely $\alpha_2\beta_1$ (collagen receptor), $\alpha_5\beta_1$ (fibronectin receptor), and $\alpha_6\beta_1$ (laminin receptor) as well as 2 $\beta_3$-integrins, $\alpha_{IIb}\beta_3$ and $\alpha_v\beta_3$, the latter only being present in very low amounts. Among them, 2 are considered to be of pivotal importance for platelet adhesion and aggregation on the exposed subendothelial matrix: $\alpha_2\beta_1$ and $\alpha_{IIb}\beta_3$.

Ruoslahti et al. have obtained a series of patents relating to RGD peptides. For example, U.S. Pat. No. 5,695,997, entitled "Tetrapeptide," relates to a method of altering cell attachment activity of cells, comprising: contacting the cells with a substantially pure soluble peptide including RGDX where X is any amino acid and the peptide has cell attachment activity. The patent further includes an embodiment where X is any amino acid and the peptide has cell attachment activity and the peptide has less than about 31 amino acids.

Koivunen et al., "Phage Libraries Displaying Cyclic Peptides with Different Ring Sizes: Ligand Specificities of the RGD-Directed Integrins," Bio/Technology 13:265-270 (1995) discloses selective ligands to the cell surface receptors of fibronectin ($\alpha_5\beta_1$ integrin), vitronectin (($\alpha_v\beta_3$ integrin and $\alpha_v\beta_5$ integrin and fibrinogen ($\alpha_m\beta_3$ integrin from phage libraries expressing cyclic peptides. A mixture of libraries was used that express a series of peptides flanked by a cysteine residue on each side (CX5C, CX6C, CX7C) or only on one side (CX9) of the insert.

Reiss et al., "Inhibition of platelet aggregation by grafting RGD and KGD sequences on the structural scaffold of small disulfide-rich proteins," Platelets 17(3):153-7 (May 2006) discloses RGD and KGD containing peptide sequences with seven and 11 amino acids, respectively, which were grafted into two cystine knot microproteins, the trypsin inhibitor EETI-II and the melanocortin receptor binding domain of the human agouti-related protein AgRP, as well as into the small disintegrin obtustatin. The peptide sequences shown are modified from native scaffold sequences, having three disulfide bonds, and $IC_{50}$ values in the micromolar range were reported.

Wu et al., "Stepwise in vitro affinity maturation of Vitaxin, an $\alpha_v\beta_3$-specific humanized mAb," *Proc. Nat. Acad. Sci.*, Vol. 95, Issue 11, 6037-6042, May 26, 1998, discloses a focused mutagenesis implemented by codon-based mutagenesis applied to Vitaxin, a humanized version of the antiangiogenic antibody LM609 directed against a conformational epitope of the $\alpha_v\beta_3$ integrin complex.

BRIEF SUMMARY OF THE INVENTION

The following brief summary is not intended to include all features and aspects of the present invention, nor does it imply that the invention must include all features and aspects discussed in this summary.

The present invention provides cystine-knot peptides engineered for specificity against $\alpha_{IIb}\beta_3$ integrin. It is also an object of the present invention to provide a method of preparing cystine-knot peptides that are engineered for specificity against $\alpha_{IIb}\beta_3$ integrin. It is, moreover, an object of the present invention to provide a method of using these cystine-knot peptides in anti-thrombotic therapies.

In certain aspects, the present invention comprises a knottin peptide binding with high affinity to $\alpha_{iib}\beta_3$ (written out as alpha IIb beta 3) integrin, having a sequence substantially identical to a sequence having an engineered loop of 9-12 residues inserted into a knottin peptide substantially identical to AgRP or AgTx. The peptide may be selected from the sequences at least 95% identical to an AgRP-scaffold based sequence GCVRLHESCLGQQVPCCDPAATCYC $X_1X_2RGDX_6X_7X_8X_9CYCR$ (SEQ ID NO: 1) or an AgTx-scaffold based sequence GCIAEDYGRCTWGGTPCCR-GRGCIC $X_1X_2RGDX_6X_7X_8X_9$ CECT (SEQ ID NO: 2), where X residues are contained in a loop region and $X_1$ is K, L, R, V, Y or N; $X_2$ is K or G $X_6$ is W, V, M or R; $X_7$ is R, K or N; $X_8$ is G, E, S, V, R, M, L, Q, or T; and $X_9$ is K, R, M or T.

In certain aspects, the present invention comprises a knottin peptide having the above-mentioned loop and scaffold, and having essentially no binding to $\alpha_v\beta_3$ (written out as alpha v beta 3) integrin.

In certain aspects, the present invention comprises a knottin peptide as set forth in the sequences above, wherein $X_6$ is W and $X_7$ and $X_9$ are each independently R or K, and being specific for $\alpha_v\beta_3$ integrin.

In certain aspects, the present invention comprises a knottin peptide binding as set forth in the sequences above, binding to both $\alpha_{iib}\beta_3$ integrin and $\alpha_v\beta_3$ integrin, wherein said loop region comprises sequence: $X_1GRGDVX_7VX_9$ (SEQ ID NO: 134), wherein $X_7$ and $X_9$ are each independently R or K.

In certain aspects, the present invention comprises peptides as described above, wherein the wherein the loop portion $X_1X_2RGDX_6X_7X_8X_9$ is selected from the group consisting of (b3a) VGRGDVRRK (SEQ ID NO: 107), (b3I) RGRGD-VKLR, (SEQ ID NO: 112), (2ba) LKRGDWKGK, (SEQ ID NO: 100), (2bj) NKRGDWRSK, (SEQ ID NO: 105), and (2bO), KKRGDWKER (SEQ ID NO: 106).

In certain aspects, the present invention comprises peptides as described above, where the scaffold is an AgRP sequence further comprising a native C-terminal portion. In certain aspects, the present invention comprises peptides as described above where the scaffold is an AgTx sequence substantially identical to a sequence represented by SEQ ID NO: 133.

In certain aspects, the present invention comprises a knottin peptide having an AgRP scaffold substantially identical to an agouti peptide, according to SEQ ID NO: 1, GCVRLHES-CLGQQVPCCDPAATCYC $X_1X_2RGDX_6X_7X_8X_9CYCR$, wherein $X_1$ is K, L, R, V, Y or N; $X_2$ is K or G $X_6$ is W, V, M or R; $X_7$ is R, K or N; $X_8$ is G, E, S, V, R, M, L, Q, or T; and $X_9$ is K, R, M or T.

In certain aspects, the present invention comprises a knottin peptide having a scaffold substantially identical to an agatoxin sequence GCIAEDYGRCTWGGTPCCRGRGCICX$_1$X$_2$RGDX$_6$ X$_7$X$_8$X$_9$CECT (SEQ ID NO: 2), wherein $X_1$ is K, L, R, V, Y or N; $X_2$ is K or G; $X_6$ is W, V, M or R; $X_7$ is R, K or N; $X_8$ is G, E, S, V, R, M, L, Q, or T; and $X_9$ is K, R, M or T.

In certain aspects, the present invention comprises a method of preventing platelet aggregation in a mammal which comprises administering an effective amount of a peptide having a sequence substantially identical to a sequence as described above. The peptide in this case may be contained in a pharmaceutical composition suitable for administration to a subject in need thereof, which may be a human in need of anti-thrombotic therapy. The pharmaceutical composition will comprise an engineered integrin binding knottin and a pharmaceutically-acceptable carrier.

In certain aspects, the present invention comprises a method for preparing a peptide specifically binding to an $\alpha_{iib}\beta_3$ integrin, and not binding to a non-$\alpha_{iib}\beta_3$ integrin, comprising the steps of: (a) preparing a library expressing a collection of peptides with different binding properties; (b) selecting from said collection peptides that bind to $\alpha_{iib}\beta_3$ integrin to obtain a positive pool; and (c) selecting and removing from said positive pool peptides that bind to said non-$\alpha_{iib}\beta_3$ integrin. These peptides may be expressed in recombinant yeast, and clones selected where they express high binding for $\alpha_{iib}\beta_3$ integrin and essentially no binding for $\alpha_v\beta_3$ integrin, or other β3 containing integrins.

DETAILED DESCRIPTION OF THE PREFERRED EMBODIMENT

Figure 1:
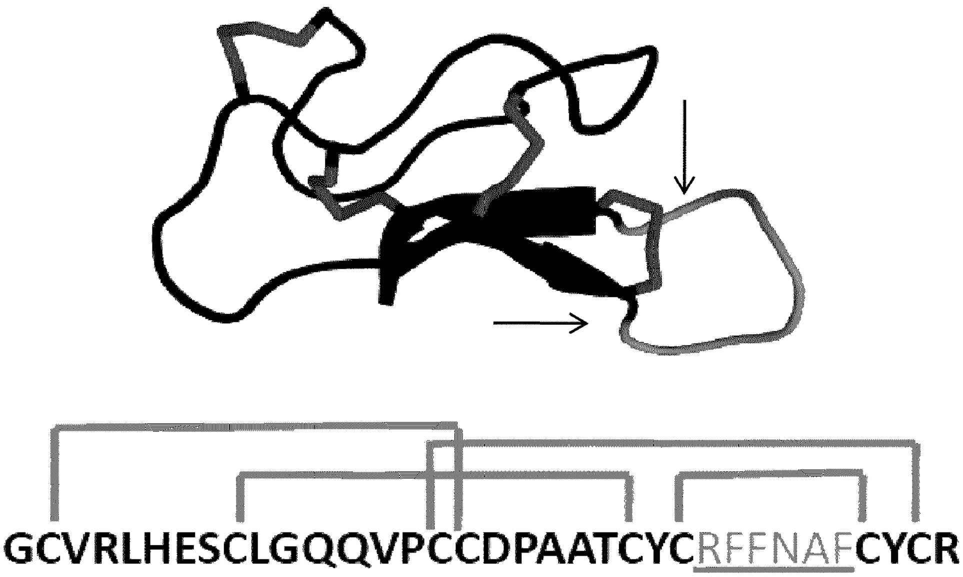
FIG. 1 illustrates the structure and sequence of the wild-type truncated form of AgRP (SEQ ID NO: 3, shown in FIG. 1). AgRP Loop 4 (RFFNAF (SEQ ID NO: 135), shown between arrows) was substituted with the sequence XXRGDXXXX, where X=any amino acid.

Overview $\alpha_{IIb}\beta_3$ integrin (also known as GPIIb-IIIa) is a glycoprotein complex found predominantly on platelets and is responsible for platelet aggregation and thrombosis. Agents that block $\beta_{IIb}\beta_3$ integrin can prevent thrombosis by preventing platelets from binding fibrinogen, fibronectin, and von Willebrand factor. They find uses in prevention and acute treatment of arterial thrombosis including restenosis, drug-eluting stents, and coronary angioplasty.

Monoclonal antibodies and other agents have long circulation times and can lead to pathological bleeding; as a result suboptimal doses must be administered and the therapeutic window is very narrow. Small molecule (oral) drugs have been unsuccessful due to increased bleeding and associated mortality. It is difficult to make specific antagonists for $\alpha_{IIb}\beta_3$ integrin that do not also bind other integrins.

The AgRP and other peptides engineered in this work are interesting due to their novel binding specificities and for their potential as therapeutic agents to inhibit thrombosis. Platelets have ~80,000 copies of $\alpha_{IIb}\beta_3$ integrin (glycoprotein IIb/IIIa) on their surface in addition to ~1000 copies each of $\alpha_2\beta_1$, $\alpha_5\beta_1$, $\alpha_6\beta_1$ integrin, and only ~100 copies of $\alpha_v\beta_3$ integrin. These integrins mediate adhesion to fibrinogen as well as von-Willebrand factor, vitronectin, and fibronectin. Prior to ligand binding, $\alpha_{IIb}\beta_3$ integrin must be activated by inside-out signaling that leads to active site conformational changes. Fibrinogen presents multiple adhesive sites, leading to platelet crosslinking via binding to activated $\alpha_{IIb}\beta_3$ integrin, resulting in clot formation.

Several compounds have been used clinically to prevent $\alpha_{IIb}\beta_3$-mediated platelet aggregation for patients at risk of thrombosis of coronary arteries after percutaneous coronary intervention (PCI). The $\alpha_{IIb}\beta_3$ integrin-specific antibody fragment c7E3, abciximab (Reopro®), was approved by the FDA in 1994 as adjunctive therapy to prevent ischemic complications of coronary artery angioplasty. Abciximab led to >90% blockage of $\alpha_{IIb}\beta_3$ integrin and >80% inhibition of ADP-induced platelet aggregation, but in spite of a 12-hour infusion, over two-thirds of the antibody persists in the patient for several weeks. This led to bleeding issues in many patients, requiring increased red blood cell and platelet transfusions. This issue is particularly relevant in patients who need to undergo emergency coronary artery bypass graft after cessation of abciximab treatment. Additionally, abciximab also binds to $\alpha_v\beta_3$ integrin and the leukocyte integrin Mac-1. While it is unclear whether or not there is any safety issue with the associated $\alpha_v\beta_3$ integrin binding, there does not appear to be any treatment benefit to targeting both of these receptors.

Eptifibatide (Integrilin®) is an $\alpha_{IIb}\beta_3$ integrin-specific cyclic heptapeptide that contains a homoargenine-glycine-aspartate sequence, and is approved to reduce the risk of acute cardiac ischemic events in patients with unstable angina or undergoing PCI. While the efficacy of eptifibatide is somewhat limited compared to abciximab in that it must be used in conjunction with other anti-platelet medications such as aspirin or clopidogrel as well as heparin, its circulation time is much shorter, such that normal platelet function is restored within 2-4 hours post-treatment. As a result, no increases in bleeding have been reported for patients administered eptifibatide versus control groups.

The engineered AgRP peptides described below have properties that compare favorably to these FDA approved drugs. In addition to high specificity for $\alpha_{IIb}\beta_3$ (see e.g. clones identified below as 2bA, 2bJ, and 2bO) or $\beta_3$ integrins (e.g. clones b3A and b3I), all of the engineered AgRP peptides performed as well or slightly better than eptifibatide in inhibiting ADP-induced platelet aggregation. It has also been shown that radiolabeled versions of the present $\alpha_v\beta_3$ integrin-binding AgRP peptides have rapid blood clearance in mice of ~10-20 minutes, but are still able to elicit high uptake in integrin-expressing tumor xenografts models using human glioma derived U87MG cells. (See, for data, Jiang, L., Kimura, R. H., Miao, Z., Silverman, A. P., Ren, G., Liu, H. G., Li, P. Y., Gambhir, S. S., Cochran, J. R., and Cheng, Z., "Evaluation of a $^{64}$Cu-Labeled Cystine-Knot Peptide Based on Agouti Related Protein for PET Imaging of Tumors Expressing $\alpha_v\beta_3$ Integrin," *Journal of Nuclear Medicine,* 51, 251-8. 2010). Therefore, it seems likely that these engineered peptides would be able to target and bind platelets in vivo, and their short half-life will be desirable for reducing the risks of bleeding and other side effects. The present engineered knottins have also shown promise for oral availability; however, thus far only injectable proteins and peptidomimetics have been proven successful, as orally administered small molecule $\alpha_{IIb}\beta_3$ antagonists appear to actually induce platelet aggregation in vivo. Platelet aggregation is measured in vitro by a number of known techniques, and an effective dosage may be determined in this way. Platelet aggregation may be measured by using a cone-and-plate aggregometer. Platelet response may also be monitored as a percentage reduction in adenosine 5'-diphosphate-induced platelet aggregation at selected days after beginning of therapy and compared with baseline.

Also of clinical interest is the role of $\alpha_{IIb}\beta_3$ integrin in tumor cell-induced platelet aggregation. Many disintegrins, cysteine-rich peptides found in snake venom, contain RGD or KGD sequences and block platelet aggregation by binding to $\alpha_{IIb}\beta_3$ integrin. Interestingly, two such $\alpha_{IIb}\beta_3$-specific disintegrins, trigramin and rhodostomin, have shown efficacy in blocking tumor cell-induced platelet aggregation, a critical component of tumor transvascular metastasis. Thus, there may be potential for using $\alpha_{IIb}\beta_3$-specific peptides, such as those described in this work, as therapeutic inhibitors of tumor metastasis.

As described in Yeh et al., "Rhodostomin, A Snake Venom Disintegrin, Inhibits Angiogenesis Elicited by Basic Fibroblast Growth Factor and Suppresses Tumor Growth by A Selective $\alpha_v\beta_3$ Blockade of Endothelial Cells," Mol. Pharm. 59(5):1333-1342 (2001), disintegrins are a family of low-molecular-weight, RGD-containing peptides that bind specifically to integrins $\alpha_{IIb}\beta_3$, $\alpha_5\beta_1$, and $\alpha_v\beta_3$ expressed on platelets and other cells including vascular endothelial cells and some tumor cells. In addition to their potent antiplatelet activity, studies of disintegrins have revealed a new use in the diagnosis of cardiovascular diseases and the design of therapeutic agents in arterial thrombosis, osteoporosis, and angiogenesis-related tumor growth and metastasis. It has been shown that disintegrin inhibited adhesion of tumor cells to extracellular matrices and in vivo experimental metastasis of B16 murine melanoma cells. Investigators have demonstrated that disintegrin inhibits either spontaneous or tumor associated angiogenesis.

As exemplified below, AgRP can be used as a scaffold for engineering peptides with different integrin specificities by mutating a single loop of the knottin peptide. These examples also indicate that creative library screening strategies can be developed and used to engineer scaffold proteins where target specificity is an issue. Additionally, AgRP peptides engineered in accordance with the present invention showed high efficacy in inhibiting platelet aggregation in vitro and have translational potential as thrombosis inhibitors.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "knottin peptide" or "cystine knot peptide" is used herein to refer to a miniprotein with a knotted topology with three to five disulfide bridges with one disulfide penetrating through a macrocycle formed by two other disulfides and inter-connecting peptide backbones. Other terms used in the art to describe these miniproteins are "knottins" or "cystine knots". Information about various known knottin peptides, such as primary sequences, 3D-structures and folding patterns as well as function, may be obtained by consulting the KNOTTIN database, which is freely available, at http (colon)//knottin(dot)cbs(dot)cnrs(dot)fr or http(colon)//knottin(dot)com.

Agouti-related protein (AgRP), a knottin peptide, contains a highly basic N-terminal region, a Pro-rich central domain and a C-terminal region rich in cysteine (Cys) residues. From the sequence, loop 4 of AgRP is between the $6^{th}$ and $7^{th}$ cysteine from the N-terminus. The same orientation may be used for other knottin peptides having the same folding pattern as AgRP. As noted below, while any of the four exposed solvent loops of the knottin peptide may be substituted with a consensus sequence of the present invention, it is generally preferred if the fourth exposed solvent loop (as defined herein) is substituted with a consensus sequence.

Miniaturized or mini as used herein for either AgRP (Agouti-related protein) or AgTx (any of the Agatoxins) means either of the AgRP or AgTx having a C-terminus portion removed. Procedures for removal of the C-terminus portion of AgRP are well-known and described in Jackson et al (2002) Biochemistry 41: 7565 and McNulty (2001) Biochemistry 40:15520. Based on the sequence for omega agatoxin, the cystine-knot domain (C-terminus removed) is approximately 38 amino acids, although this may differ slightly for other agatoxins. The present inventors have obtained miniaturized AgRP using the procedure of Jackson et al. AgTx was miniaturized (C-terminus removed) by performing a sequence alignment with AgTx and mini-AgRP, and performing the analogous truncation.

The cystine knot portion of the AgRP is residues 87-132, which is itself the C-terminal portion of the natural AgRP. What is referred to herein as mini-AgRP has been truncated to AgRP (87-120, C105A). Thus residues 121-132 are analogous to the C-terminus portion of AgTx.

The term "amino acid" includes both naturally occurring and synthetic amino acids and includes the D and L form of the acids as well as the racemic form. More specifically, amino acids contain up to ten carbon atoms. They may contain an additional carboxyl group, and heteroatoms such as nitrogen and sulfur. Preferably the amino acids are α and β-amino acids. The term α-amino acid refers to amino acids in which the amino group is attached to the carbon directly attached to the carboxyl group, which is the α-carbon. The term β-amino acid refers to amino acids in which the amino group is attached to a carbon one removed from the carboxyl group, which is the β-carbon. The amino acids described here are referred to in standard IUPAC single letter nomenclature, with "X" meaning any amino acid.

The term "AgRP" means PDB entry 1HYK. Its entry in the Knottin database is SwissProt AGRP_HUMAN. It has the sequence GCVRLHESCLGQQVPCCDPCATCYCRFFNAFCYCR-KLGTAMNPCSRT (SEQ ID NO: 132).

The dashed portion shows a C terminal fragment omitted in the "mini" version, below. The bold and underlined sequence above and in the sequences below represents a loop portion that is replaced with an integrin binding sequence that is not native to the knottin, but is created artificially as described below.

Disulfide bonds are between cysteines 1-16, 8-22, 15-33, 19-43, and 24-31 in the native sequence. The native sequence does not contain the added N terminal glycine and thus begins with Cys 1.

The term "mini" in reference to AgRP means PDB entry 1MRO. It is also SwissProt AGRP_HUMAN. It has the sequence, similar to that given above, GCVRLHESCLGQQVPCCDPAATCYCRFFNAFCYCR (SEQ ID NO: 3) where the italicized "A" represents an amino acid substitution which eliminates a possible dimer forming cystine. The native disulfide bond (cys19-cys43) is missing because of this substitution and the omission of the C-terminal fragment. (Cysteine herein refers to the single amino acid; cystine to the dimer.) The bold and underlined sequence above and in the sequences below represents a loop portion that is replaced with an integrin binding sequence that is not native to the knottin, but is created artificially as described below.

Thus, the term AgRP, as used here to refer to a scaffold for an integrin binding loop, as indicated above, can include a "native AgRP," with 5 disulfide bonds, an engineered AgRP that has all 46 residues, plus an additional residue, e.g. G at the N terminus and a Cys replacement with a neutral residue such as Val, Ala or Gly; a "mini" AgRP that has the C-terminal portion omitted as shown above, as well as a modified N-terminus and modified Cys content.

The term "agatoxin" means omega agatoxin PDB 1OMB and the SwissProt entry in the knottin database TOG4B_AGEAP. It has the sequence EDN-CIAEDYGKCTWGGTKCCRGRPCRCSMIGTNCECT-PRLIMEGLSFA (SEQ ID NO: 133).

The dashes indicate N- and C-terminal portions of the peptide omitted for the "mini" agatoxin. As shown in Table 3, an additional glycine is added to the N-terminus of the mini-construct.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window, which in this case is either the entire peptide, a molecular scaffold portion, or a binding loop portion (~9-11 residues). Preferably, optimal alignment is conducted using the homology alignment algorithm of Needleman and Wunsch (1970) *J. Mol. Biol.,* 48:443 453. An indication that two peptide sequences are substantially identical is that one peptide is immunologically reactive with antibodies raised against the second peptide. Another indication for present purposes, that a sequence is substantially identical to a specific sequence explicitly exemplified is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified, e.g., by the PAM 250 scoring matrix. Peptides that are "substantially identical" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (http (colon) slash slash helixweb(dot)nih (dot) gov/multi-align/). Three-dimensional tools may also be used for sequence comparison.

To determine if a peptide is substantially identical to a given sequence, one will first identify the loop region apart from the scaffold region. The loop region will be defined within 1-2 amino acids that can be varied, i.e. 1/9 residues or about 89% percentage sequence identity. Furthermore, the sequence RGD may not be varied, unless replaced by an equivalent sequence as discussed below. The scaffold sequence can tolerate greater diversity (e.g. 30/37 or about 80% percentage sequence identity) provided that the topology is maintained by intramolecular bonds. This will generally require that the cysteine residues remain unchanged in identity and sequence register, i.e. spacing within the peptide and spacing relative to the cysteine locations.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A sequence identity may be specified by percentage to allow certain substitutions, with the proviso that amino acid identities in the proviso are not changed.

The term "anti-thrombotic therapy" is used as it is conventionally understood by those in the art, and refers to the use of platelet aggregation inhibitors in treating occlusive vascular disease. For example, WO 95/12412 discloses platelet-specific chimeric antibodies and methods of using the same in treating various thrombotic disorders. A prototype description of the efforts to develop this therapeutic agent and obtain approval for its use as a human therapeutic agent (generic name: abciximab, trade name: ReoPro®) was described by B. S. Coller in Circulation 92:2373 (1995).

The term "high affinity" means having an equilibrium binding constant ($K_D$; 50% maximum binding) between the peptide and integrin ligand in soluble form of less than 100 nM. High affinity may also include $K_D$'s of less than about 60 nM or less than about 30 nM. Contrariwise, essentially no affinity would be essentially no binding at 250 nM.

General Methods and Materials

1. General Considerations

The present invention provides peptide scaffolds into which are inserted engineered sequences that bind specifically to integrins such as $\alpha_{IIb}\beta_3$ integrin and $\alpha_v\beta_3$ integrin with high affinity. The peptides have fast clearance, but since the molecules are very high affinity (e.g. less than 100 nanomolar), they potentially have a broader therapeutic window. Exemplary features of the present peptides are:

1) peptides that are highly specific for $\alpha_{IIb}\beta_3$ (alpha IIb beta III) integrin over $\alpha_v\beta_3$ (alpha v beta III) integrin, or bind to both, and have high affinity, in the nanomolar range;

2) peptides that are serum-stable and are non-immunogenic;

3) peptides where a loop of a known knottin scaffold, such as AgRP (Agouti-Related Protein) or AgTx (Agatoxin) is replaced with an engineered sequence at a loop region, where the native sequence is replaced with 5-10 amino acids which include the RGD or;

4) modifications to knottin scaffolds, e.g. where a truncated-Agouti-related protein is substituted with a loop of 5-10 amino acids, which amino acids include the RGD sequence, or related specific integrin binding sequence such as KGD. U.S. Pat. No. 5,519,005, to Ofer et al., relates to certain non-peptidic compounds comprising a guanidino and a carboxyl terminal groups with a spacer sequence of 11 atoms between them, which are effective inhibitors of cellular or molecular interactions which depend on RXD or DGR recognition, wherein X is G (gly), E (glu), Y (tyr), A (ala) or F (phe). These RXD and DGR analogues are referred to as "RXD surrogates."

2. Selection of Peptides

According to the present methods, randomized inserts such as XXRGDXXXX, where X is any amino acid, were cloned into cysteine knot peptides and expressed on the surface of yeast. The resulting library was screened using yeast surface display and FACS for peptides that bound $\alpha_{IIb}\beta_3$ integrin; to maximize specificity, negative selection was also performed against $\alpha_v\beta_3$ integrin. The substituted loop for the $\alpha_{IIb}\beta_3$ integrin-specific peptides had the consensus sequence: $XKRGDWX_7XX_9$, (SEQ ID NO: 4) where X=variable amino acids and $X_{7,9}$=Arg or Lys. The substituted loop for the peptides that bind both $\alpha_{IIb}\beta_3$ integrin and $\alpha_v\beta_3$ integrin had the consensus sequence XGRGDV $X_7XX_9$, (SEQ ID NO: 5) where X=variable amino acids and $X_{7,9}$ Arg or Lys. The consensus sequences described herein can be used with both AgRP and AgTx.

The present engineered AgRP or AgTx variants were identified from a loop-substituted yeast display library where clones were selected for binding to $\alpha_{IIb}\beta_3$ integrin. Fluorescence-activated cell sorting was used. Using different yeast sorting strategies, AgRP variants were isolated with specificity for either $\alpha_{IIb}\beta_3$ or for both integrins having a $\beta_3$ subunit. When produced in soluble form, the engineered peptides bound to cellular integrins with high affinities and expected specificities. In addition, it was determined that the engineered peptides serve as potent inhibitors of platelet aggregation.

A constrained six amino acid loop in AgRP was replaced with a nine amino acid loop containing an Arg-Gly-Asp integrin recognition motif, and the neighboring residues were randomized, to create a library of 20 million AgRP mutants. These AgRP mutants were displayed as fusions on the surface of yeast and used high-throughput fluorescence-activated cell sorting (FACS) to isolate AgRP variants that bound the platelet integrin $\alpha_{IIb}\beta_3$. Several rounds of library screening were performed solely against $\alpha_{IIb}\beta_3$ integrin and it was found that the isolated AgRP peptides bound with high affinity both $\alpha_{IIb}\beta_3$ and the related $\alpha_{IIb}\beta_3$ integrin, presumably through specificity of the $\beta_3$ subunit. By adopting a strategy of alternating positive sorting for binding to $\alpha_{IIb}\beta_3$ integrin with negative sorting against binding to $\alpha_v\beta_3$ integrin, a second set of AgRP peptides with high affinity and specificity for $\alpha_{IIb}\beta_3$ integrin ($\alpha_{IIb}\beta_3$-specific peptides) was isolated.

The specificities of the engineered AgRP peptides were measured against cell surface expressed integrin receptors. The $\alpha_{IIb}\beta_3$-specific peptides bound $\alpha_{IIb}\beta_3$ integrin with $K_D$ values from 59-87 nM and did not bind to $\alpha_v\beta_3$, $\alpha_v\beta_5$, or $\alpha_5\beta_1$ integrins. In comparison, the $\beta_3$-specific peptides bound $\alpha_{IIb}\beta_3$ and $\alpha_v\beta_3$ integrins with $K_D$ values ranging from 40-70 nM and 23-28 nM, respectively, and did not bind to $\alpha_v\beta_5$ or $\alpha_5\beta_1$ integrins. Unique consensus sequences were identified within both series of peptides and were used to offer potential insight into molecular recognition events that dictate different integrin binding specificities. In addition, we showed that the engineered AgRP peptides prevented platelet aggregation as well as or slightly better than the FDA-approved cyclic peptide eptifibatide. Collectively, these data demonstrates that cystine-knot peptides can be generated with high affinity, specificity, and functional efficacy against closely-related and clinically-significant integrin receptors and suggests that this engineering approach may be extended to develop targeting peptides against other receptors of interest.

3. Peptide Sequences

The engineered AgRP and AgTx peptides were recombinantly produced in *Pichia pastoris*, a yeast expression system providing high yields and eukaryotic folding capability, to produce proper folding and intramolecular disulfide bonds. Using recombinant techniques, the present sequences can be varied as desired. In addition, the peptides can be produced as fusion proteins with other proteins or protein domains. For example, an engineered $\alpha_{IIb}\beta_3$-specific knottin peptide such as disclosed here could be prepared as part of a larger sequence attached to the N- or C-terminus encoding a protein or protein domain that is to be directed to platelets or megakaryocytes, or an adjunct protein such as the thrombolytic, tissue plasminogen activator. The present knottin peptides can be prepared as multimers, or in clusters. Also, a knottin peptide as described here could be coupled to a radiolabel for imaging.

Below is an exemplary list of peptide sequences from the cystine-knot peptides of the present invention that first binds both $\alpha_{IIb}\beta_3$ and second that bind both $\alpha_{IIb}\beta_3$ and $\alpha_v\beta_3$, i.e. in Tables 1 and 2, respectively. As described above, these peptides contain portions of the native AgRP which is CVRLHESCLGQQVPCCDPCATCYCRFFNAFCYCRKLGTAMNPCSRT (SEQ ID NO: 6).

TABLE 1

| AgRP peptides that bind BOTH $\alpha_{IIb}\beta_3$ and $\alpha_y\beta_3$: | |
|---|---|
| 5A | GCVRLHESCLGQQVPCCDPAATCYCVGRGDVRRKCYCR (SEQ ID NO: 7) |
| 5I | GCVRLHESCLGQQVPCCDPAATCYCVGRGDMDRRCYCR (SEQ ID NO: 8) |
| 5J | GCVRLHESCLGQQVPCCDPAATCYCKGRGDVKRECYCR (SEQ ID NO: 9) |
| 5E | GCVRLHESCLGQQVPCCDPAATCYCRGRGDVNVKCYCR (SEQ ID NO: 10) |
| 5F | GCVRLHESCLGQQVPCCDPAATCYCRGRGDMNRKCYCR (SEQ ID NO: 11) |
| 5B | GCVRLHESCLGQQVPCCDPAATCYCRGRGDVKMRCYCR (SEQ ID NO: 12) |
| 5G | GCVRLHESCLGQQVPCCDPAATCYCRGRGDTKMKCYCR (SEQ ID NO: 13) |
| 5C | GCVRLHESCLGQQVPCCDPAATCYCSGRGDVRMRCYCR (SEQ ID NO: 14) |
| 5K | GCVRLHESCLGQQVPCCDPAATCYCSGRGDVRMRCYCR (SEQ ID NO: 15) |
| 5H | GCVRLHESCLGQQVPCCDPAATCYCMGRGDVKLRCYCR (SEQ ID NO: 16) |
| 5D | GCVRLHESCLGQQVPCCDPAATCYCMGRGDTDMKCYCR (SEQ ID NO: 17) |
| 5L | GCVRLHESCLGQQVPCCDPAATCYCKSRGDVKVKCYCR (SEQ ID NO: 18) |
| 6A | GCVRLHESCLGQQVPCCDPAATCYCVGRGDVKMKCYCR (SEQ ID NO: 19) |
| 6L | GCVRLHESCLGQQVPCCDPAATCYCVGRGDVKRKCYCR (SEQ ID NO: 20) |
| 6G | GCVRLHESCLGQQVPCCDPAATCYCVGRGDMRRKCYCR (SEQ ID NO: 21) |
| 6E | GCVRLHESCLGQQVPCCDPAATCYCLGRGDVKRRCYCR (SEQ ID NO: 22) |
| 6B | GCVRLHESCLGQQVPCCDPAATCYCSGRGDVRMRCYCR (SEQ ID NO: 23) |
| 6D | GCVRLHESCLGQQVPCCDPPATCYCYGRGDVKMRCYCR (SEQ ID NO: 24) |
| 6F | GCVRLHESCLGQQVPCCDPAATCYCYGRGDVKMRCYCR (SEQ ID NO: 25) |

TABLE 1-continued

| AgRP peptides that bind BOTH $\alpha_{IIb}\beta_3$ and $\alpha_v\beta_3$: | |
|---|---|
| 6C | GCVRLHESCLGQQVPCCDPAATCYCRGRGDVKMVCYCR (SEQ ID NO: 26) |
| 6I | GCVRLHESCLGQQVPCCDPAATCYCRGRGDVKLKCYCR (SEQ ID NO: 27) |
| 6K | GCVRLHESCLGQQVPCCDPAATCYCRGRGDVKLRCYCR (SEQ ID NO: 28) |
| 6J | GCVRLHESCLGQQVPCCDPAATCYCRGRGDTKMKCYCR (SEQ ID NO: 29) |
| 7A | GCVRLHESCLGQQVPCCDPAATCYCVGRGDVRRKCYCR (SEQ ID NO: 30) |
| 7E | GCVRLBESCLGQQVPCCDPAATCYCRGRGDVRRKCYCR (SEQ ID NO: 31) |
| 7D | GCVRLHESCLGQQVPCCDPAATCYCKGRGDVRMKCYCR (SEQ ID NO: 32) |
| 7B | GCVRLHESCLGQQVPCCDPAATCYCYGRGDVKMRCYCR (SEQ ID NO: 33) |
| 7F | GCVRLHESCLGQQVPCCDPAATCYCRGRGDVKMRCYCR (SEQ ID NO: 34) |
| 7I | GCVRLHESCIGQQVPCCDPAATCYCRGRGDVKLRCYCR (SEQ ID NO: 35) |
| 7P | GCVRLHESCLGQQVPCCDPAATCYCRGRGDVKVRCYCR (SEQ ID NO: 36) |
| 7N | GCVRLHESCLGQQVPCCDPAATCYCRGRGDVKLKCYCR (SEQ ID NO: 37) |
| 7L | GCVRLHESCLGQQVPCCDPAATCYCRGRGDVKRICYCR (SEQ ID NO: 38) |
| 7K | GCVRLHESCLGQQVPCCDPTATCYCKGRGDMRRRCYCR (SEQ ID NO: 39) |
| 7G | GCVRLHESCLGQQVPCCDPAATCYCVGRGDVNTRCYCR (SEQ ID NO: 40) |
| 7C | GCVRLHESCLGQQVPCCDPAATCYCIGRGDRKQRCYCR (SEQ ID NO: 41) |

Note the consensus XGRGDVX$_7$XX$_9$, (SEQ ID NO: 5), where X = any amino acid and X$_{7,9}$ = R or K

TABLE 2

| AgRP peptides that bind ONLY to $\alpha_v\beta_3$ | |
|---|---|
| 25A | GCVRLHESCLGQQVPCCDPAATCYCRKRGDWRGMCYCR (SEQ ID NO: 42) |
| 25D | GCVRLHESCLGQQVPCCDPAATCYCGKRGDWKGKCYCR (SEQ ID NO: 43) |
| 25E | GCVRLHESCLGQQVPCCDPAATCYCNKRGDWRSKCYCR (SEQ ID NO: 44) |
| 25F | GCVRLHESCLGQQVPCCDPAATCYCYKRGDWKSRCYCR (SEQ ID NO: 45) |
| 25B | GCVRLHESCLGQQVPCCDPAATCYCKKRGDWREACYCR (SEQ ID NO: 46) |
| 25L | GCVRLHESCLGQQVPCCDPAATCYCKKRGDWREACYCR (SEQ ID NO: 47) |
| 25C | GCVRLHESCLGQQVPCCDPAATCYCKKRGDWKEECYCR (SEQ ID NO: 48) |

TABLE 2-continued

| AgRP peptides that bind ONLY to $\alpha_v\beta_3$ | |
|---|---|
| 25H | GCVRLHESCLGQQVPCCDPAATCYCVKRGDRKEKCYCR (SEQ ID NO: 49) |
| 25K | GCVRLHESCLGQQVPCCDPAATCYCVKRGDRKEKCYCR (SEQ ID NO: 50) |
| 25J | GCVRLHESCLGQQVPCCDPAATCYCKKRGDRKEECYCR (SEQ ID NO: 51) |
| 25G | GCVRLHESCLGQQVPCCDPAATCYCPKRGDERVRCYCR (SEQ ID NO: 52) |
| 25I | GCVKLHESCLGQQVPCCDPAATCYCPRRGDEKHKCYCR (SEQ ID NO: 53) |
| 26A | GCVRLHESCLGQQVPCCDPAATCYCLKRGDWKEKCYCR (SEQ ID NO: 54) |
| 26H | GCVRLHESCLGQQVPCCDPAATCYCNKRGDWKDKCYCR (SEQ ID NO: 55) |
| 26L | GCVRLHESCLGQQVPCCDPAATCYCKKRGDWREACYCR (SEQ ID NO: 56) |
| 26C | GCVRLRESCLGQQVPCCDPAATCYCRKRGDWRGMCYCR (SEQ ID NO: 57) |
| 26G | GCVRLHESCLGQQVPCCDPAATCYCRKRGDWRGMCYCR (SEQ ID NO: 58) |
| 26K | GCVRLHESCLGQQVPCCDPAATCYCRKRGDWRGMCYCR (SEQ ID NO: 59) |
| 26B | GCVRVHESCLGQQVPCCDPAATCYCWARCDWREKCYCR (SEQ ID NO: 60) |
| 26D | GCVRLHESCLGQQVPCCDPAATCYCRLRGDVKWLCYCR (SEQ ID NO: 61) |
| 26E | GCVRLHESCLGQQVPCCDPAATCYCRRRGDEKWGCYCR (SEQ ID NO: 62) |
| 26F | GCVRLHESCLGQQVPCCDPAATCYCKTRGDRKMRCYCR (SEQ ID NO: 63) |
| 26J | GCVRLHESCLGQQVPCCDPAATCYCKRRZDVKMTCYCR (SEQ ID NO: 64) |
| 26I | GCVRLHESCLGQQVPCCDPAATCYCPKRGDRKVWCYCR (SEQ ID NO: 65) |
| 27A | GCVRLHESCLGQQVPCCDPAATCYCNVKGDWGERCYCR (SEQ ID NO: 66) |
| 27B | GCVKLHESCLGQQVPCCDPAATCYCGKRGDWRGRCYCR (SEQ ID NO: 67) |
| 27J | GCVRLHESCLGQQVPCCDPAATCYCKKRCDWKGHCYCR (SEQ ID NO: 68) |
| 27C | GCVRLHESCLGQQVPCCDPAATCYCLKRGDWKEKCYCR (SEQ ID NO: 69) |
| 27E | GCVRLHESCLGQQVPCCDPAATCYCLKKGDWKGKCYCR (SEQ ID NO: 70) |
| 27P | GCVRLHESCLGQQVPCCDPAATCYCNKRGDWKDKCYCR (SEQ ID NO: 71) |
| 27K | GCVRLHESCLGQQVPCCDPAATCYCIKRGDWRGVCYCR (SEQ ID NO: 72) |
| 27F | GCVRLHESCLGQQVPCCDPAATCYCRKRCDVKWDCYCR (SEQ ID NO: 73) |
| 27I | GCVRLHESCLGQQVPCCDPAATCYCKRRGDLDWLCYCR (SEQ ID NO: 74) |

TABLE 2-continued

| AgRP peptides that bind ONLY to $\alpha_v\beta_3$ | |
|---|---|
| 27H | GCVRLHESCLGQQVPCCDPAATCYCRRRGDLKPLCYCR (SEQ ID NO: 75) |
| 27M | GCVRLHESCLGQQVPCCDPAATCYCKCKGDRRCKCYCR (SEQ ID NO: 76) |
| 28A | GCVRLHESCLGQQVPCCDPAATCYCMKRGDWRGVCYCR (SEQ ID NO: 77) |
| 28C | GCVRLHESCLGQQVPCCDPAATCYCLKRGDWRGKCYCR (SEQ ID NO: 78) |
| 28K | GCVRLRESCLGQQVPCCDPAATCYCLKRGDWKGKCYCR (SEQ ID NO: 79) |
| 28F | GCVRLHESCLGQQVPCCDPAATCYCRKRGDWRGMCYCR (SEQ ID NO: 80) |
| 28G | GCVRLHESCLGQQVPCCDPAATCYCKKRGDWRGRCYCR (SEQ ID NO: 81) |
| 28I | GCVRLHESCLGQQVPCCDPAATCYCKKRGDWRSKCYCR (SEQ ID NO: 82) |
| 28B | GCVRLHESCLGQQVPCCDPAATCYCRKRGEWKDECYCR (SEQ ID NO: 83) |
| 28M | GCVRLHESCLGQQVPCCDPAATCYCRKRGCWKMVCYCR (SEQ ID NO: 84) |
| 28N | GCVRLHESCLGQQVPCCDPAATCYCRKRGDWKATCYCR (SEQ ID NO: 85) |
| 28O | GCVRLHESCLGQQVPCCDPAATCYCKKRGDWRVTCYCR (SEQ ID NO: 86) |
| 28E | GCVRLHESCLGQQVPCCDPAATCYCRKRGDVRSRCYCR (SEQ ID NO: 87) |
| 28J | GCVRLHESCLGQQVPCCDPAATCYCRRRGCVKNKCYCR (SEQ ID NO: 88) |
| 29A | GCVRLHESCLGQQVPCCDPAATCYCLKRGDWKGKCYCR (SEQ ID NO: 89) |
| 29C | GCVRLHESCLGQQVPCCDPAATCYCLKRGDWRGRCYCR (SEQ ID NO: 90) |
| 29B | GCVRLHESCLGQQVPCCDPAATCYCRKRGDWRGMCYCR (SEQ ID NO: 91) |
| 29K | GCVRLHESCLGQQVPCCDPAATCYCKKRGDWRGRCYCR (SEQ ID NO: 92) |
| 29H | GCVRLHESCLGQQVPCCDPAATCYCKKRGDWRVKCYCR (SEQ ID NO: 93) |
| 29J | GCVRLHESCLGQQVPCCDPAATCYCNKRGDWRSKCYCR (SEQ ID NO: 94) |
| 29O | GCVRLHESCLGQQVPCCDPAATCYCKKRGDWKERCYCR (SEQ ID NO: 95) |

As stated, either AgRP or AgTx may be used as a cystine-knot peptide scaffold upon which to make the described sequence substitutions. If AgTx is selected, any one of the known Agatoxins may be used, however, the C-terminus portion of each is preferably removed before use in order to preclude toxicity. The C-terminus may be removed in accordance with conventional procedures. Both AgRP and AgTx with or without the C-terminus portion may be used interchangeably in view of their identical or similar folding patterns.

4. Tertiary Structures and Variations

The present knottin scaffolds may be varied in sequence while preserving the important three dimensional structure of the scaffold. One may use, for example, AgTx variants that have homologous 3D structures to AgRP. For example, there are Agatoxin IVA and Agatoxin IVB variants that have different sequences, but they are structurally homologous. In fact, when the pattern of Cys residues and disulfide bonds is conserved, then the structure will be similar with a folding pattern identical or similar to AgRP. What is important is the 3D topology of the loop in question which is formed by the structure.

1AGG is the PDB database entry for OMEGA-AGA-TOXIN-IVB. This polypeptide has the sequence EDNCIAEDYGKCTWGGTKCCRGRPCRCSMIGTNCECTPRLIMEGLSFA (SEQ ID NO: 96).

Another agatoxin sequence that may be used is 1OAV. 1OAV is the PDB entry for OMEGA-AGATOXIN IVA. It has the amino acid sequence KKKCIAKDYGRCKWGGTPCCRGRGCICSIMGTNCECKPRLIMEGLGLA (SEQ ID NO: 97).

The two versions of agatoxin A and B, while very close in knottin part, differ much more in the termini, and thus have different interactions and activities with the calcium channels.

Any AgTx variant may be used as a scaffold for carrying a consensus sequence as disclosed hereinabove, provided that the AgTx variant has a folding pattern that is of the same type as the AgTx folding pattern. Protein folding is the physical process by which a polypeptide folds into its characteristic and functional three-dimensional structure from the polypeptide primary structure, i.e., amino acid sequence. Usually, folded proteins have a hydrophobic core in which side chain packing stabilizes the folded state, and charged or polar side chains occupy the solvent-exposed surface where they interact with surrounding water.

Exemplary and well-known techniques for studying protein folding include circular dichroism, dual polarization interferometry, energy landscape theory of protein folding and computational predictions of protein tertiary structure. X-ray crystallography and NMR may also be mentioned.

Additionally, attention is also directed to U.S. Pat. No. 5,680,319, entitled "Hierarchical protein folding prediction," which, as is noted at the end of the specification, is incorporated herein by reference. This patent describes one method of predicting the three-dimensional structure of a protein fragment and could be used for varying scaffold sequences. As noted above, the loop sequences may be randomized and selected by binding affinity, according to the methods taught here.

Generally, the following guidelines may be used in preparing consensus sequence-substituted AgTx variants for use in accordance with the present invention:

1) Select an AgTx variant minus the C-terminus portion having the same folding pattern as AgTx using any known technique for determining protein folding patterns, including using the KNOTTIN database;
2) Insert a consensus sequence (as disclosed hereinabove) at the same corresponding special loci on the AgTx variant (the substituted AgTx variant may be prepared synthetically by solid-phase synthesis or by fermentation). It is sufficient if the loci initially selected is within 10-20 amino acid residues (on either side) of the preferred actual loci;
3) Determine binding specificity for the modified AgTx variant as described in the present specification; and 4) Adjust the location of the consensus sequence in the AgTx variant to obtain the preferred binding specificity.

Generally, any of the agatoxins may be used as scaffolds provided that it has the same or similar folding pattern as AgRP. Any of the alpha-, mu- or omega-agatoxins may be selected for further suitability. An example of an alpha variant is AG 489. Of the mu-variants, subtypes 1, 2, 3, 4, 5, and 6 may be noted having 36, 37, 38, 37, 37 and 37 amino acids, respectively. Examples of omega variants include, for example, subtypes IA, IB, IIA, IIB, IIIA, IIIB, IIIC, IIID, IVA and IVB with amino acid lengths varying from 48 to 112 amino acids. By 'further suitability' is meant determining the folding pattern based on known methodologies and then conducting studies to determine the preferred loci for placing any of the disclosed consensus sequences described hereinabove.

5. Formulations

The present invention also encompasses a pharmaceutical composition useful in the treatment or prevention of undesirable thrombi, e.g. in treatment of individuals who suffer from coronary artery disease or injury following myocardial infarction, atherosclerosis, arteriosclerosis, preeclampsia, embolism, platelet-associated ischemic disorders including lung ischemia, coronary ischemia, and cerebral ischemia, and for the prevention of reocclusion following thrombosis, thrombotic disorders including coronary artery thrombosis, cerebral artery thrombosis, intracardiac thrombosis, peripheral artery thrombosis, venous thrombosis, thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surface, in combination with angioplasty, carotid endarterectomy, anastomosis of vascular grafts, and chronic cardiovascular devices such as in-dwelling catheters or shunts. Other instances in which it would be useful to inhibit increased ADP release due to increased platelet stimulation would be in individuals at high risk for thrombus formation or reformation (severe arteriosclerosis), and inhibition of occlusion, reocclusion, stenosis and/or restenosis of blood vessels.

The present invention contemplates the administration of a therapeutically effective amount of the present peptides, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a peptide according to this invention is administered into a human subject, the daily dosage will normally be determined by the prescribing physician with the dosage generally varying according to the age, weight, and response of the individual patient, as well as the severity of the patient's symptoms.

In one exemplary application, administration occurs in an amount between about 0.1 mg/kg of body weight to about 60 mg/kg of body weight per day, preferably of between 0.5 mg/kg of body weight to about 40 mg/kg of body weight per day.

The pharmaceutical composition may be administered parenterally, topically, orally or locally. It is preferably given by parenteral, e.g., subcutaneous, intradermal or intramuscular route, preferably by subcutaneous or intradermal route, in order to reach platelets.

The composition according to the invention for parenteral administration is generally in the form of a solution or suspension of the peptide in a pharmaceutically acceptable carrier, preferably an aqueous carrier. Examples of aqueous carriers that may be used include water, buffered water, saline solution (0.4%), glycine solution (0.3%), hyaluronic acid and similar known carriers. Apart from aqueous carriers it is also possible to use solvents such as dimethylsulphoxide, propyleneglycol, dimethylformamide and mixtures thereof. The composition may also contain pharmaceutically acceptable excipients such as buffer substances and inorganic salts in order to achieve normal osmotic pressure and/or effective lyophilization. Examples of such additives are sodium and potassium salts, e.g., chlorides and phosphates, sucrose, glucose, protein hydrolysates, dextran, polyvinylpyrrolidone or polyethylene glycol. The compositions may be sterilized by conventional methods, e.g., by sterile filtration. The composition may be decanted directly in this form or lyophilized and mixed with a sterile solution before use.

The present peptides will be administered in a manner to prevent or minimize platelet aggregation in a subject at risk for thrombosis or other disorders involving unwanted platelet aggregation. A patient in need of the present platelet integrin binding peptides may receive, e.g. an 135-μg/kg-200 μg/kg intravenous loading dose and 0.5 μg/kg per minute by intravenous infusion. It should be administered in an effective dosage to cause competitive inhibition of binding of fibrinogen, Von Willebrand factor and other adhesive ligands, to resting and active GP IIb/IIIa receptors. With recommended dosage, peak plasma drug concentration should occur within about 5 minutes of injection and steady-state drug concentration is 1.5-2.2 μg/ml. The peptides are formulated for intravenous (i.v.) administration in the strength of 0.75 mg/ml and 2 mg/ml (10 ml vial) as a clear, colorless, sterile solution. The vial should be stored under refrigeration between 2-8° C. and protected from light until administration.

EXAMPLES

Example 1

Materials and Methods

Library Synthesis and Screening

The AgRP loop 4 random library was prepared as described in J. Mol. Biol. 385, 1064-1075. Briefly, the AgRP gene was assembled by overlap extension PCR using Taq polymerase in the presence of DMSO. Primers were used that contained NNS degenerate codons in place of loop 4, where N=A, C, T or G and S=C or G, which codes for all 20 amino acids and the TAG stop codon. The assembled gene was PCR amplified using end primers with 40 bp overlap to the pCT vector upstream and downstream of the NheI and BamHI restriction sites for homologous recombination in yeast. Digested pCT vector (0.5-1 μg) and amplified linear gene product (5-10 μg) were electroporated into the *S. cerevisiae* strain EBY100, yielding a library of ~$2\times10^7$ transformants. See Nat. Biotech. 15: 553-557, regarding EBY100.

The yeast library was grown in selective media (SD-CAA, 20 g/L glucose, 6.7 g/L yeast nitrogen base without amino acids, 5.4 g/L $N\alpha_2HPO_4$, 8.6 g/L $NaH_2PO_4.H_2O$, and 5 g/L Bacto casamino acids) and induced in selective media containing galactose (SG-CAA). For library screening, 5 to $25\times10^6$ yeast (depending on the sort round) were labeled with detergent-solubilized integrin and a 1:250 dilution of chicken anti-c-myc IgY (Invitrogen) in integrin binding buffer (IBB, 20 mM Tris pH 7.5 with 1 mM $MgCl_2$, 1 mM $MnCl_2$, 2 mM $CaCl_2$, 100 mM NaCl, and 1 mg/mL bovine serum albumin) at room temperature for 2 h. The yeast cells were centrifuged at 4° C. and the supernatant was removed by aspiration. The yeast were then resuspended in ice-cold BPBS (PBS containing 1 mg/mL bovine serum albumen) containing a 1:100 dilution of phycoerythrin-conjugated goat anti-chicken IgY secondary antibody (Santa Cruz Biotechnology) and a 1:25 dilution of either fluorescein-conjugated anti-$\alpha_v\beta_3$ antibody (Biolegend) or fluorescein-conjugated anti-$\alpha_{IIb}$ antibody (Biolegend), as appropriate. After incubation for 20 min on ice, the yeast were centrifuged, aspirated, and stored as pellets on ice until cell sorting. Yeast library screening was performed using a Becton Dickinson FACS Vantage SE instrument (Stanford FACS Core Facility) and CellQuest software. In positive sort rounds, 1-2% of yeast cells that best bound to $\alpha_{IIb}\beta_3$ integrin were collected using a diagonal sort gate to normalize binding with protein expression levels. For negative sort rounds, the 1-2% of yeast cells that expressed AgRP peptides but showed the weakest binding to $\alpha_v\beta_3$ integrin were collected. The isolated yeast clones were propagated in SD-CAA media, induced for AgRP expression in SG-CAA media, and subjected to additional rounds of FACS.

Detergent-solubilized $\alpha_{IIb}\beta_3$ integrin (human GPIIb/IIIa) was obtained from Enzyme Research as a Triton X-100 formulation. Detergent-solubilized $\alpha_v\beta_3$ integrin was purchased from Millipore as an octyl-β-D-glucopyranoside formulation. Seven rounds of positive-only sorts were performed using the following concentrations of $\alpha_{IIb}\beta_3$ integrin:—round 1: 250 nM, round 2: 250 nM, round 3: 100 nM, round 4: 50 nM, round 5: 50 nM, round 6: 25 nM, round 7: 10 nM. In a separate sorting strategy, nine rounds of varying positive and negative sorts were performed using the following concentrations of integrin: round 1: 250 nM $\alpha_{IIb}\beta_3$, round 2: 250 nM $\alpha_{IIb}\beta_3$, round 3: 100 nM $\alpha_v\beta_3$ (negative sort), round 4: 100 nM $\alpha_v\beta_3$ (negative sort), round 5: 50 nM $\alpha_{IIb}\beta_3$, round 6: 100 nM $\alpha_v\beta_3$ (negative sort), round 7: 100 nM $\alpha_v\beta_3$ (negative sort), round 8: 25 nM $\alpha_{IIb}\beta_3$, round 9: 25 nM $\alpha_{IIb}\beta_3$. Plasmid DNA was recovered from yeast clones using a Zymoprep kit (Zymo Research) and transformed into XL-1 blue supercompetent *E. coli* cells (Stratagene) for plasmid miniprep. DNA sequencing of resulting clones was performed by MCLab (South San Francisco, Calif.).

Recombinant Production of Engineered AgRP Peptides

Recombinant AgRP peptides were prepared using the Multi-Copy Pichia Expression Kit (Invitrogen) following the manufacturer's instructions. The open reading frames of the AgRP peptide genes were cloned into the pPIC9K plasmid, which also contained N-terminal FLAG and C-terminal hexahistidine epitope tags (SEQ ID NO: 136) as handles for integrin binding measurements and peptide purification. Plasmid (5-10 □g) was linearized by digestion with SacI and electroporated into the *P. pastoris* strain GS115. Yeast cells were then streaked onto YPD plates containing 4 mg/mL geneticin to select for cells containing multiple insertions. Individual colonies were tested for AgRP peptide expression by Western blot after probing the membrane with an antibody against the FLAG epitope tag. Scale-up was performed in 500 mL liquid cultures over 3 days while maintaining the concentration of methanol at ~0.5% to induce AgRP peptide production. The crude yeast supernatants were adjusted to pH 8.0, filtered, and AgRP peptides were purified by affinity chromatography using Ni-NTA beads. Following concentration and buffer exchange to PBS using Amicon Ultra Centrifugation tubes (3 kDa cutoff, Millipore), the AgRP peptides were further purified by size exclusion chromatography using a Superdex-75 gel filtration column (GE Healthcare). Masses of purified peptides were confirmed by matrix-assisted laser desorption/ionization time-of-flight (MALDI-TOF) mass spectrometry and concentrations were determined from absorbance readings at 270 nm and previously determined extinction coefficients. Additionally, the purity of the peptides, as well as the presence or absence of multimers was assayed with SDS-PAGE using 4-12% Bis-Tris gels that were stained with SimplyBlue Safestain (Invitrogen).

Cell Binding Assays

K562 cells stably expressing $\alpha_{IIb}\beta_3$, $\alpha_v\beta_3$, or $\alpha_v\beta_5$ were obtained from S. Blystone and maintained in IMDM media (Gibco) containing 10% FBS and 1.0 mg/mL geneticin. For binding assays, $10^5$ cells were suspended in IBB, and varying concentrations of AgRP peptides were added. After 3 hour incubation at 4° C., the cells were centrifuged, aspirated, and resuspended in ice-cold BPBS containing a 1:20 dilution of fluorescein-conjugated goat anti-His antibody (Bethyl) for 20 on ice. The cells were then centrifuged, aspirated, and stored as pellets on ice until analysis by flow cytometry using a BD FACS Caliber instrument Becton Dickinson. Binding data was analyzed with FlowJo (Treestar, Inc.) and data was fit to sigmoidal plots using Kaleidagraph (Synergy Software) to calculate equilibrium dissociation constants. Experiments were performed at least 3 times and data are presented as average values with standard deviations.

Platelet Aggregation Assays

Human platelets isolated by pheresis were obtained from the Stanford Blood Center and stored in serum with 7% acid/citrate/dextrose (ACD) solution. Prior to use, the platelets were centrifuged, aspirated, washed once with Tyrode's buffer (140 mM NaCl, 3 mM KCl, 12 mM $NaHCO_3$, 0.4 mM $NaH_2PO_4$, 2 mM $MgCl_2$, 0.1% glucose, pH 7.4), and counted using a haemacytometer. Counted platelets were resuspended in fresh plasma to a final concentration of approximately $2.8\times10^8$ cells/mL. 180 μL of the platelet solution, or approximately $5\times10^7$ platelets, were added to separate wells in a 96-well microtiter plate. AgRP peptide or eptifibatide (Cell Sciences) were added to the wells at varying concentrations, after which the platelets were activated with 25 μM ADP. Absorbance at 365 nm was monitored over 1 hr using a Synergy 4 microplate reader (BioTek Instrumentation) with readings taken every 35 s, with 3 s of shaking between readings. The end points for each concentration of peptide tested were plotted as percentage of maximum inhibition versus log peptide concentration, and $IC_{50}$ values were calculated by fitting this data to sigmoidal curves. Experiments were performed at least 3 times.

Example 2

Engineering Integrin-Binding AgRP Peptides

Figure 2:
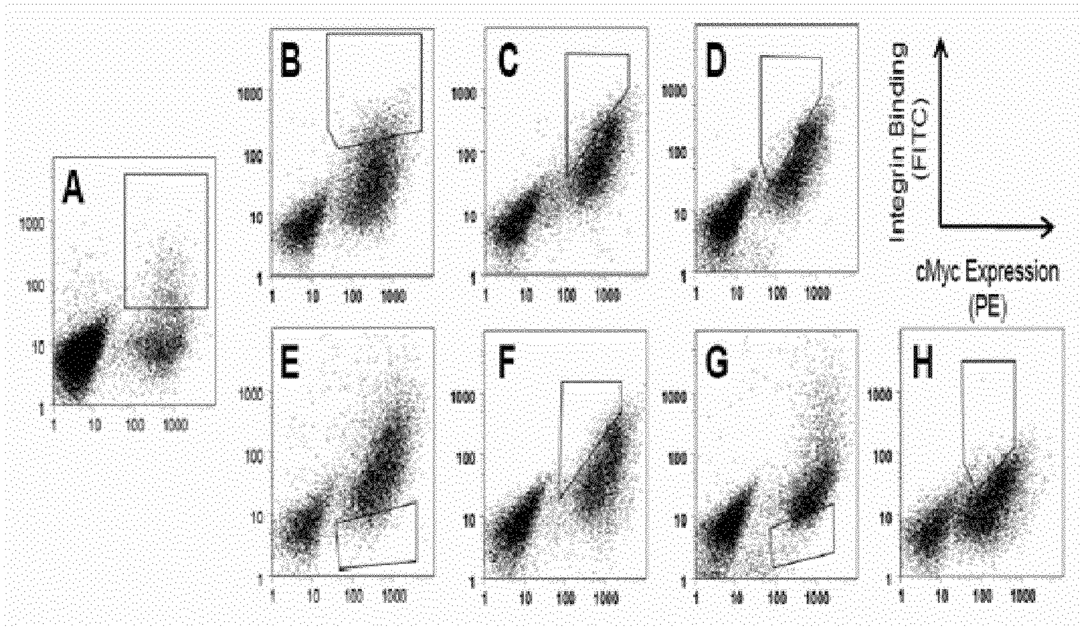
FIG. 2 A-H is a series of dot plots that illustrates FACS screening of the yeast-displayed AgRP loop 4 libraries. Boxed areas within the plots show the population of yeast cells collected in each sort. (A) Sort round 1, 250 nM $\alpha_{IIb}\beta_3$ integrin. (B)-(D) Succession of positive-only sort rounds carried out against $\alpha_{IIb}\beta_3$ integrin. (B) Round 3, 100 nM $\alpha_{IIb}\beta_3$. (C) Round 5, 50 nM $\alpha_{IIb}\beta_3$. (D) Round 7, 10 nM $\alpha_{IIb}\beta_3$. (E)-(H) Succession of varying positive and negative sort rounds performed against $\alpha_{IIb}\beta_3$ and $\alpha_v\beta_3$, integrin respectively. (E) Round 3 (negative sort), 100 nM $\alpha_v\beta_3$. (F) Round 5 (positive sort), 50 nM $\alpha_{IIb}\beta_3$. (G) Round 6 (negative sort), 100 nM $\alpha_v\beta_3$. (H) Round 9 (positive sort), 25 nM $\alpha_{IIb}\beta_3$. X axis indicates AgRP peptide expression, measured by detection of the C-terminal cMyc epitope tag using an anti-cMyc primary antibody and phycoerythrin (PE)-conjugated secondary antibody. Y axis indicates integrin binding, measured by incubation with the indicated concentration of detergent-solubilized integrin, followed by fluorescein (FITC)-conjugated anti-integrin antibody.

Yeast surface display was used to engineer integrin binding knottin peptides, a technique previously described in the literature in connection with other peptides. It was found that the technique provided ease of performing high-throughput, quantitative library screens using fluorescence-activated cell sorting (FACS). Using degenerate codons, loop 4 AgRP (FIG. 1: RFFNAF (SEQ ID NO: 135)) was replaced with the sequence XXRGDXXXX, where X represents any amino acid. This approach resulted in a library of AgRP variants that contained the RGD integrin-recognition sequence with randomized flanking residues. RGD was placed in position 3 of the loop because gross molecular modeling of sequences derived from the RGD-containing loop of fibronectin demonstrated that substitution of the loop sequence TGRGDSPAS (SEQ ID NO: 98) into AgRP loop 4 gave the greatest structural similarities to the original fibronectin loop. Homologous recombination of mutant AgRP DNA and linearized yeast display plasmid pCT in the *S. cerevisiae* strain EBY100 afforded a library of ~$20^7$ transformants. The AgRP peptide variants were expressed as fusions to the yeast cell wall protein Aga2 under the control of a galactose promoter and contained a C-terminal cMyc epitope tag (EQKLI-SEEDL) (SEQ ID NO: 99) for detection and quantification of peptide expression levels using an anti-cMyc antibody. Next, the yeast-displayed AgRP library was screened to isolate mutants that were well expressed on the yeast cell surface and bound with high affinity to detergent-solubilized $\alpha_{IIb}\beta_3$ integrin. In the initial sort round, $5\times10^7$ yeast were labeled with 250 nM $\alpha_{IIb}\beta_3$ integrin and a chicken anti-cMyc antibody for 2 h at room temperature. After washing, the cells were resuspended in ice-cold BPBS containing a fluorescein-conjugated anti-$\alpha_{IIb}$ antibody and a PE-conjugated anti-chicken antibody. Following incubation with these secondary antibodies, the yeast libraries were sorted by FACS. Approximately 1-2% yeast cells that displayed AgRP peptides (as measured through cMyc expression levels) and showed the highest binding to $\alpha_{IIb}\beta_3$ integrin were collected using a rectangular sort gate, (FIG. 2A). The collected cells were grown in selective media and induced for AgRP expression then the sorting process was repeated against $\alpha_{IIb}\beta_3$ integrin.

Figure 3:
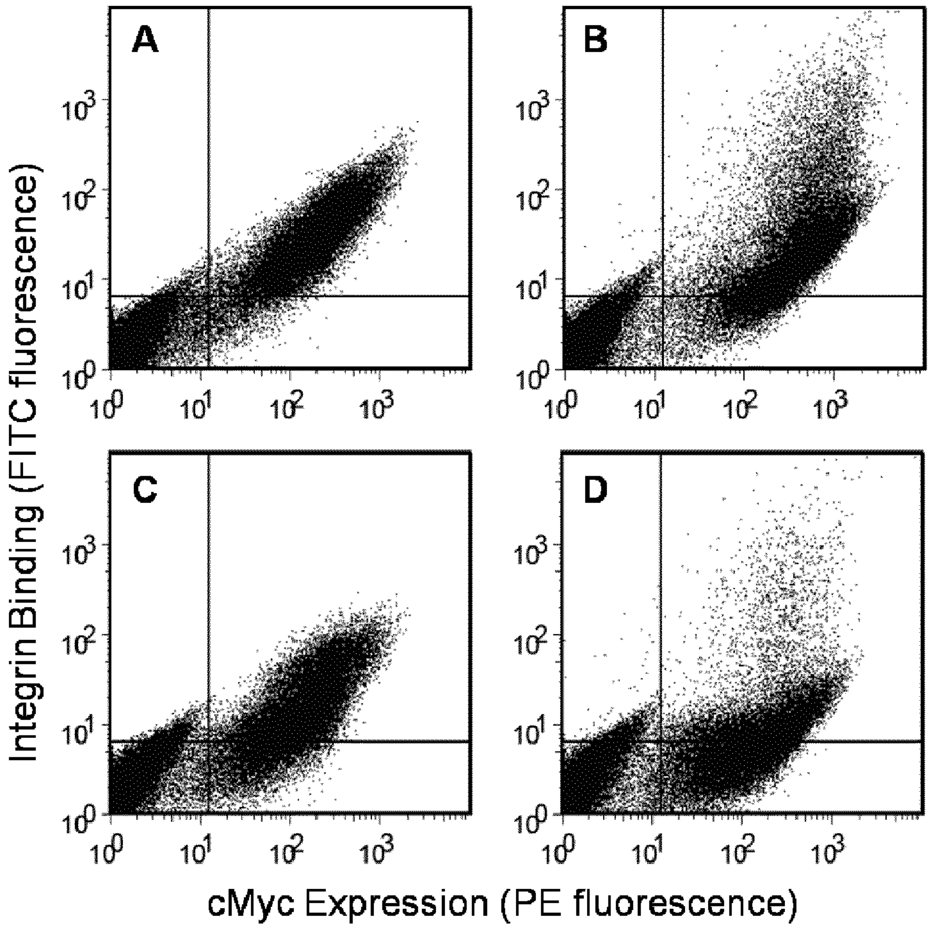
FIG. 3 A-D is a series of dot plots that illustrate pools of enriched yeast analyzed after library screening by FACS. (A and B) Yeast-displayed AgRP peptides screened for binding to $\alpha_{IIb}\beta_3$ integrin only. (C and D) Yeast-displayed AgRP peptides alternately screened for binding to $\alpha_{IIb}\beta_3$ integrin and for lack of binding to $\alpha_v\beta_3$ integrin. (A and C) Binding to 25 nM $\alpha_{IIb}\beta_3$ integrin. (B and D) Binding to 25 nM $\alpha_v\beta_3$ integrin. Quadrants are shown to facilitate comparison between populations.
Figure 7:
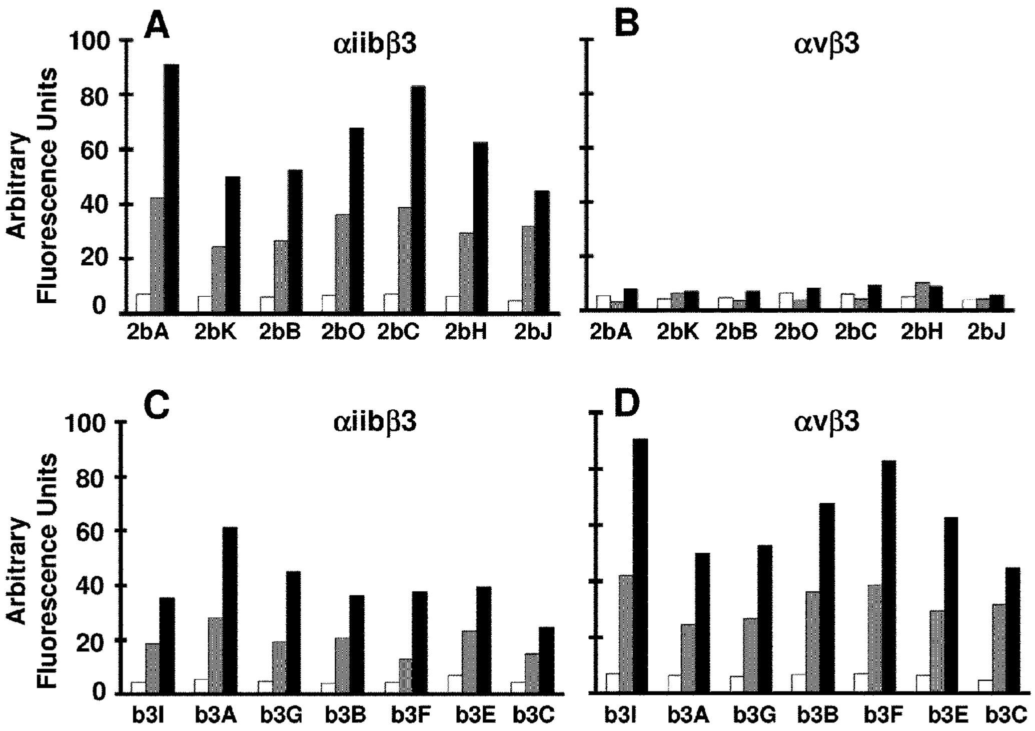
FIG. 7 A-D is a series of bar graphs that illustrate binding specificity of individual yeast-displayed AgRP mutants as described in plots A, B, C and D. (A-B) $\alpha_{IIb}\beta_3$-specific peptides, (C-D) β3-specific peptides. (A) and (C) Binding to 1 nM □, 10 nM ▒ or 50 nM ■ $\alpha_{IIb}\beta_3$ integrin. (B) and (D) Binding to 10 nM □, 50 nM ▒, or 100 nM ■ $\alpha_v\beta3$ integrin.

After the second round of FACS, the pooled yeast clones were tested for binding to 100 nM $\alpha_{IIb}\beta_3$ or $\alpha_v\beta_3$ integrin; this assay revealed, that our library screening approach was enriching for yeast-displayed AgRP peptides that bound to both $\alpha_{IIb}\beta_3$ and $\alpha_v\beta_3$ integrins. Consequentially, we revised our sorting strategy to take a two-pronged approach. In one set of experiments we sorted only against $\alpha_{IIb}\beta_3$, presumably leading to a set of knottin peptides enriched for binding $\beta_3$ integrin-subunits. In an alternative approach, we interspersed negative sorting against $\alpha_v\beta_3$ with positive sorting against $\alpha_{IIb}\beta_3$ in order to improve the likelihood of isolating knottin peptides specific for $\alpha_{IIb}\beta_3$ integrin. We performed a total of 7 rounds of positive-only sort against $\alpha_{IIb}\beta_3$ integrin (FIG. 2B-D), enriching the population such that the final sort round was performed with 10 nM $\alpha_{IIb}\beta_3$ integrin. In this strategy, a diagonal sort gate was used to collect the yeast clones that bound the most integrin for a given level of peptide expression, thereby normalizing peptide expression and integrin binding. In the alternative sorting sequence, in rounds 3, 4, 6, and 7, the yeast-displayed AgRP peptides were incubated with 100 nM $\alpha_v\beta_3$ and the cMyc-expressing population that bound the worst to $\alpha_v\beta_3$ integrin was collected (FIGS. 2E and G), whereas in sorts 5, 8, and 9 the yeast were sorted for binding to $\alpha_{IIb}\beta_3$ (FIGS. 2F and H). For all sorts, approximately 1-2% of the yeast population was collected. The resulting peptide populations showed expected specificities when tested on the yeast surface: the population sorted only for binding to $\alpha_{IIb}\beta_3$ (hereafter to be referred to as $\beta_3$-specific clones) bound $\alpha_{IIb}\beta_3$ and $\alpha_v\beta_3$ integrins similarly, while the population of peptides that was alternately sorted for $\alpha_{IIb}\beta_3$-positive and $\alpha_v\beta_3$-negative binding (hereafter to be referred to as $\alpha_{IIb}\beta_3$-specific clones) showed strong preference for $\alpha_{IIb}\beta_3$ over $\alpha_v\beta_3$ integrin (FIG. 3). Additionally, selected individual clones from each set of sorts showed the expected integrin binding specificities (FIG. 7).

Figure 4:
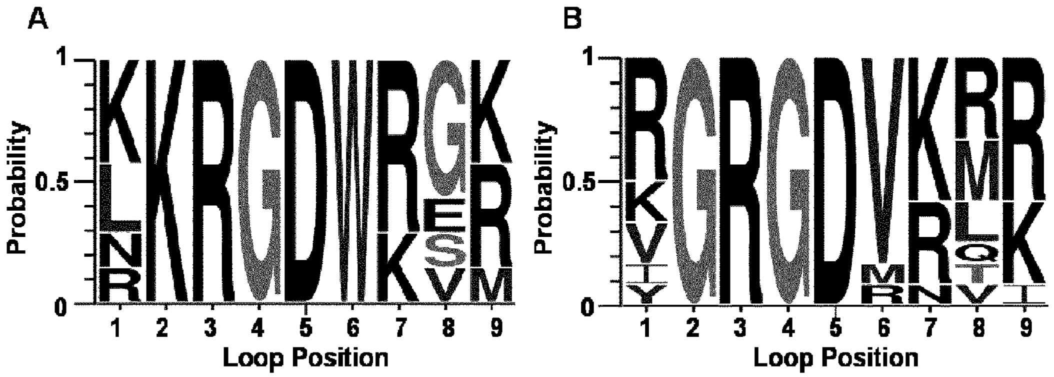
FIGS. 4 A and B are graphics that illustrate relative amino acid of mutations found in each position of AgRP loop 4 (SEP ID NOS 143 and 144, respectively, in order of appearance) from clones isolated after the final round of library screening. Images were generated with Weblogo software (weblogo (dot)berkeley.edu). The amplitude of residues at a given position indicates their frequency of occurrence. (A) $\alpha_{IIb}\beta_3$-specific peptides, 7 unique sequences used as input. (B) $\beta_3$-specific peptides, 12 unique sequences used as input.
Figure 5:
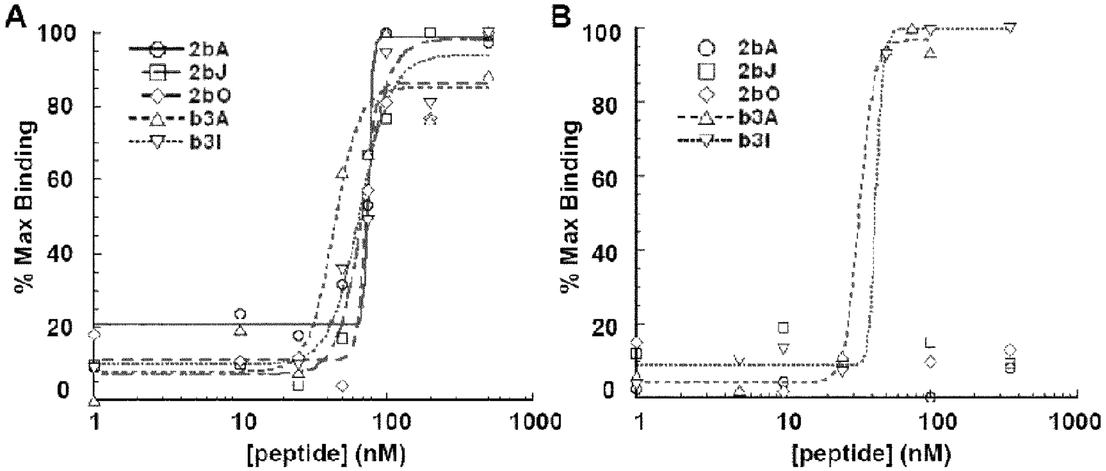
FIGS. 5 A and B are line graphs that illustrate binding titrations of engineered AgRP peptides to cell lines expressing integrin receptors. (A) K562-αIIbβ3 cells. (B) K562-αvβ3 cells. Data show % maximum binding for cells incubated with various concentrations of AgRP peptides. Binding was detected using a fluorescin-conjugated anti-hexahistidine antibody ('hexahistidine' disclosed as SEQ ID NO: 136) and flow cytometry analysis. Representative data from three repetitions are shown.

Sixteen individual clones each were sequenced from the $\alpha_{IIb}\beta_3$-specific and $\beta_3$-specific populations, revealing 7 and 12 unique sequences, respectively. The loop 4 sequences of the engineered AgRP peptides are shown in Table 3, along with the loop 4 sequences of $\alpha_v\beta_3$-specific AgRP peptides engineered in our prior study for comparison See J. Mol. Biol. 385, 1064-1075. In FIG. 4, the distribution of amino acid frequencies at each position is shown as a WebLogo image See Genome Research 14, 1188-1190 (2004). Consensus sequences for AgRP loop 4 emerged for peptides identified from both library sorting strategies. The $\alpha_{IIb}\beta_3$-specific peptides have the consensus sequence X-K-R-G-D-W-(K/R)-X-(K/R) (SEQ ID NO: 4), while the $\beta_3$-specific peptides have the consensus sequence X-G-R-G-D-V-(K/R)-X-(K/R) (SEQ ID NO: 5), where X indicates that a variety of amino acids were found at that position. Interestingly, both populations have a (K/R)-X-(K/R) motif at the C-terminus of the loop. In comparison, the previously reported $\alpha_v\beta_3$-specific AgRP peptides did not indicate such a strong consensus, but all mutants had a Gly residue immediately preceding the RGD-sequence and four of five mutants had an Asp or Gln residue immediately following the RGD (Table 3).

Table 3. Sequences of AgRP loop 4 from selections for $\alpha_{IIb}\beta_3$-specific binders or $\beta_3$-specific binders. Sequences are from clones isolated after the final sort round and ordered based on multiple sequence alignment tool Multalin.

| | | |
|---|---|---|
| $\alpha_{IIb}\beta_3$-specific peptides | | |
| 2bA | LKRGDWKGK | (SEQ ID NO: 100) |
| 2bC | LKRGDWRGR | (SEQ ID NO: 101) |
| 2bB | RKRGDWRGM | (SEQ ID NO: 102) |
| 2bK | KKRGDWRGR | (SEQ ID NO: 103) |
| 2bH | KKRGDWRVK | (SEQ ID NO: 104) |
| 2bJ | NKRGDWRSK | (SEQ ID NO: 105) |
| 2bO | KKRGDWKER | (SEQ ID NO: 106) |
| $\beta_3$-specific peptides | | |
| b3A | VGRGDVRRK | (SEQ ID NO: 107) |
| b3E | RGRGDVRRK | (SEQ ID NO: 108) |
| b3D | KGRGDVRMK | (SEQ ID NO: 109) |
| b3B | YGRGDVKMR | (SEQ ID NO: 110) |
| b3F | RGRGDVKMR | (SEQ ID NO: 111) |
| b3I | RGRGDVKLR | (SEQ ID NO: 112) |
| b3P | RGRGDVKVR | (SEQ ID NO: 113) |
| b3N | RGRGDVKLK | (SEQ ID NO: 114) |
| b3L | RGRGDVKRI | (SEQ ID NO: 115) |
| b3K | KGRGDMRRR | (SEQ ID NO: 116) |
| b3G | VGRGDVNTR | (SEQ ID NO: 117) |
| b3C | IGRGDRKQR | (SEQ ID NO: 118) |
| $\alpha_v\beta_3$-specific peptides | | |
| 7A | SGRGDNDLV | (SEQ ID NO: 119) |
| 7B | KGRGDARLQ | (SEQ ID NO: 120) |
| 7C | YGRGDNDLR | (SEQ ID NO: 121) |
| 7E | VGRGDDNLK | (SEQ ID NO: 122) |
| 7J | EGRGDRDMK | (SEQ ID NO: 123) |

Initially the yeast-displayed AgRP loop 4 library was screened against $\alpha_{IIb}\beta_3$ integrin, and after two rounds of flow cytometric sorting for clones with $\alpha_{IIb}\beta_3$ integrin binding, the binding were nearly equally enriched as clones with $\alpha_v\beta_3$ integrin binding. This result was particularly striking considering the high degree of specificity achieved from the library when it was screened solely against $\alpha_v\beta_3$ integrin. Therefore, to isolate AgRP peptides with high specificity to $\alpha_{IIb}\beta_3$ integrin, a strategy of varying positive sorts against $\alpha_{IIb}\beta_3$ with negative sorts against $\alpha_v\beta_3$ integrin was adopted. A separate set of sorts against $\alpha_{IIb}\beta_3$ integrin alone was also performed. From these two library screening strategies as well as our previous work, there are engineered AgRP variants that fall into three specificity classes: $\alpha_v\beta_3$-specific (prior work), $\alpha_{IIb}\beta_3$-specific, and $\beta_3$-specific.

The latter two classes show distinct consensus sequences in the engineered loops (FIG. 4 and Table 3) that may help explain the origin of the specificity of these peptides. Both the $\alpha_{IIb}\beta_3$-specific and $\beta_3$-specific peptides have the sequence (K/R)-X-(K/R) at the C-terminus of the loop, while the $\alpha_v\beta_3$ peptides lack this consensus. It therefore seems plausible that the (K/R)-X-(K/R) motif is at least partly responsible for interactions with the $\alpha_{IIb}$ subunit. Basic residues found on the fringes of the binding pocket in the $\alpha_{IIb}$ subunit such as Asp232 could be involved in electrostatic interactions with one of these positively charged residues. Alternatively, the (K/R)-X-(K/R) sequence might be involved in conformationally orienting the RGD sequence for selective $\alpha_{IIb}$ subunit binding.

Selectivity for the $\alpha_{IIb}\beta_3$ integrin by eptifibatide, a cyclic heptapeptide that contains a homoarginine-glycine-aspartate sequence, is achieved in part by the ability of the homoarginine residue to reach deep into the β-propeller binding pocket of the $\alpha_{IIb}$ subunit to hydrogen bond with $\alpha_{IIb}$-Asp224; the corresponding hydrogen bonding partners for the $\alpha_v$ subunit are Asp150 and Asp218, which are in a much shallower pocket. Similarly, enhanced $\alpha_{IIb}\beta_3$-specificity for antibodies and peptides containing KGD versus RGD sequences may be due to the extension of the longer carbon chain of lysine into the deeper binding pocket of the $\alpha_{IIb}$ subunit. The homoarginine residue in eptifibatide has a carbon chain the same length as lysine and presumably allows deeper penetration into the $\alpha_{IIb}$ subunit binding pocket than normal arginine or lysine. In the future, it would interesting to determine whether replacing arginine with lysine or homoarginine in the engineered AgRP peptides would confer additional affinity to $\alpha_{IIb}\beta_3$ integrin. It is also worth noting that there is a Lys residue immediately preceding the RGD sequence in the $\alpha_{IIb}\beta_3$-specific AgRP peptides. Though it is possible that this Lys residue could extend deep into the $\alpha_{IIb}$ subunit binding pocket, this might cause steric interference with the neighboring Arg residue. More likely, this Lys is restricted from the shallower $\alpha_v$ subunit binding pocket, leading to a positioning of the RGD motif that is unfavorable for binding to $\alpha_{IIb}\beta_3$-integrin.

Both the $\alpha_{IIb}\beta_3$-specific AgRP peptides engineered in this work and eptifibatide have a Trp residue immediately following their RGD sequence. Computational and experimental studies have shown that the presence of an aromatic residue immediately after the RGD sequence in disulfide-bound cyclic peptides can confer affinity and specificity for $\alpha_{IIb}\beta_3$ integrin. However, in contrast to these reports, fibronectin analogs with the consensus sequence R-G-D-W-X-E (SEQ ID NO: 137) were shown to have enhanced affinity and specificity for $\alpha_v\beta_3$ over $\alpha_{IIb}\beta_3$ integrin. These conflicting examples illustrate the importance of the particular scaffold in determining how the binding loop is presented to its receptor. One notable structural difference between $\alpha_v\beta_3$ over $\alpha_{IIb}\beta_3$ integrins is that $\alpha_v$-binding pocket residue Asp218 is replaced in the $\alpha_{IIb}$ subunit by Phe231, which increases the hydrophobicity of the pocket. Another aromatic residue on the surface of the $\alpha_{IIb}$-binding pocket, Phe160, is positioned to potentially allow π-stacking with aromatic residues immediately following the RGD sequence. These structural differences support the observation that aromatic residues contribute to specificity for $\alpha_{IIb}\beta_3$ integrin and may explain how the Trp residue following the RGD motif in eptifibatide and certain AgRP peptides helps confer affinity and specificity for $\alpha_{IIb}\beta_3$ integrin.

The $\beta_3$-specific AgRP peptides described in this work also have consensus residues immediately flanking the RGD motif, namely the sequence G-R-G-D-V (SEQ ID NO: 138), while most of the $\alpha_v\beta_3$-specific peptides have the sequence G-R-G-D-(N/D) (SEQ ID NO: 139). A flexible residue such as Gly immediately preceding the RGD sequence may be necessary to allow the Arg residue to properly orient in the shallow $a_v$-binding pocket. The hydrophobic Val residue immediately following the RGD sequence (along with the C-terminal (K/R)-X-(K/R) consensus) is likely responsible for promoting $\alpha_{IIb}$ subunit binding. In contrast, the more hydrophilic Asn or Asp residue and, the absence of the (K/R)-X-(K/R) consensus sequence, appears to confer AgRP peptides with a preference for $\alpha_v\beta_3$ integrin.

Example 3

Expression of Engineered Peptides in *P. pastoris*

Figure 8:
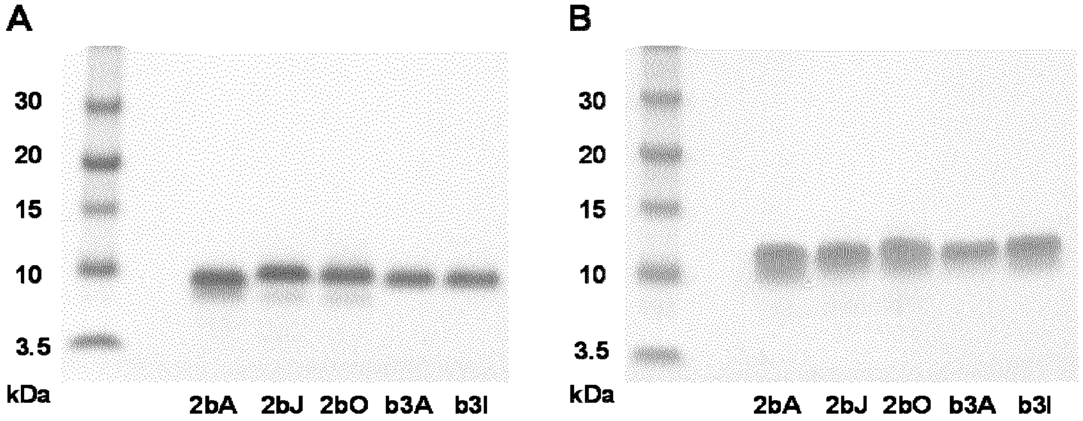
FIGS. 8 A and B are gels that illustrate SDS-PAGE analysis of AgRP mutants after Ni affinity column purification and gel filtration chromatography. (A) Reducing gel and (B) Non-reducing gel. Novex 4-12% Bis-Tris gels, run in MES buffer and stained with SimplyBlueSafestain (Invitrogen). Note that the peptides migrate slightly higher than their expected masses.

Clones 2bA, 2bJ, and 2bO (from the $\alpha_{IIb}\beta_3$-specific series), and b3A and b3I (from the $\beta_3$-specific series), were chosen for further study. When displayed on yeast, these knottin peptides exhibited the best binding to detergent-solubilized $\alpha_{IIb}\beta_3$ or $\alpha_v\beta_3$ integrin or were representative of the observed sequence diversity (Table 3 and FIG. 7). *Pichia pastoris* was used for recombinant expression as it was previously shown that this system could be used to secrete folded engineered AgRP peptides in high yield. AgRP peptides were produced with an N-terminal FLAG epitope tag (DYKDDDDK) (SEQ ID NO: 124) and a C-terminal hexahistidine tag (HHHHHH) (SEQ ID NO: 136) for use as handles in purification and cell binding assay. It was previously shown that these tags do not affect the ability of engineered AgRP peptides to bind to integrin receptors. Folded AgRP peptides were purified from the yeast supernatant by Ni-affinity chromatography as mainly monomeric species followed by size exclusion chromatography to remove any aggregates or higher order oligomers. Purified yields were approximately 1-3 mg or peptide per 500 mL of culture. The purified peptides were further characterized by MALDI-TOF mass spectrometry and reduced and nonreduced SDS-PAGE (FIG. 8 and Table 4).

TABLE 4

Matrix-assisted laser desorption/ionization time-of-flight (MALDI-TOF) mass spectrometry analysis of AgRP peptides.

| Peptide | Expected Mass (Da) | Determined Mass (Da) |
|---|---|---|
| b3A | 6790 | 6786 |
| b3I | 6804 | 6804 |
| 2bA | 6835 | 6831 |
| 2bJ | 6894 | 6891 |
| 2bO | 6950 | 6949 |

Example 4

Integrin Binding Affinity and Specificity of Engineered AgRP Peptides

To determine the integrin binding affinities and specificities of the engineered AgRP peptides, direct binding assays were performed using K562 leukemia cells that have been transfected to stably express different integrin receptors See J.

Cell Biol. 127(4) (1994). Cells were incubated in the presence of varying concentrations of AgRP peptides at 4° C., to minimize receptor internalization, followed by staining with a fluorescein-conjugated anti-hexahistidine antibody and analysis by flow cytometry. Equilibrium dissociation constants ($K_D$ values) were determined by plotting AgRP peptide concentration (log scale) versus normalized mean fluorescence intensity, then fitting the data to a sigmoidal curve.

The engineered AgRP peptides were first tested against wild-type K562 cells, which naturally express $\alpha_5\beta_1$ integrin. The peptides did not bind to these cells at concentrations up to 1 μM (data not shown). Next the binding of engineered AgRP peptides to K562 cells transfected to express $\alpha_{IIb}\beta_3$, $\alpha_v\beta_3$, or $\alpha_v\beta_5$ integrins was tested. The peptides did not bind to the K562-$\alpha_v\beta_5$ cells at concentrations up to 1 μM. Binding data for K562-$\alpha_{IIb}\beta_3$ and K562-$\alpha_v\beta_3$ cells are presented in FIG. 4 and Table 5. The engineered AgRP peptides exhibited the expected integrin binding specificities clones 2bA, 2bJ, and 2bO bound K562-$\alpha_{IIb}\beta_3$ cells only, while clones b3A and b3I bound both K562-$\alpha_{IIb}\beta_3$ and K562-$\alpha_v\beta_3$ cells. The $K_D$ values for binding to K562-$\alpha_{IIb}\beta_3$ cells varied by only 2-fold, ranging from 42-87 nM for all clones. Interestingly, clones b3A and b3I both had even higher affinity for the K562-$\alpha_v\beta_3$ cells compared to K562-$\alpha_{IIb}\beta_3$ cells, with $K_D$ value around 25 nM.

Example 5

Engineered AgRP Peptides Inhibit Platelet Aggregation

Figure 6:
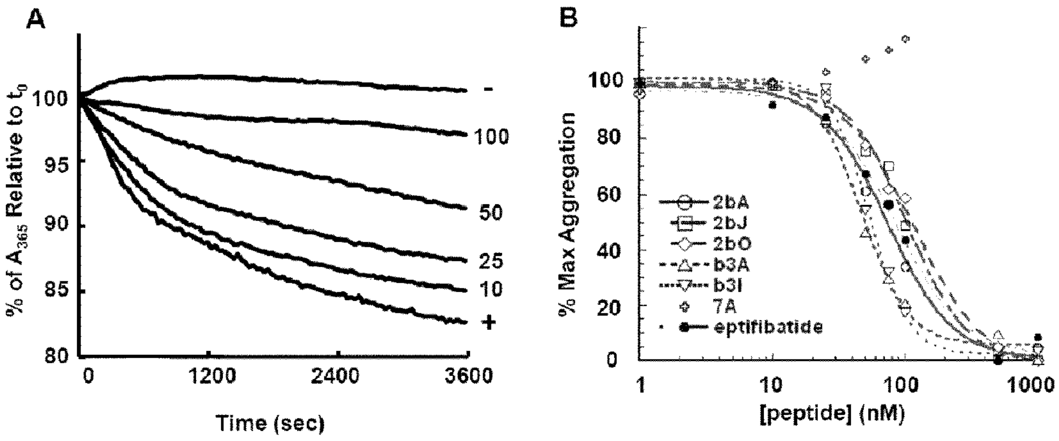
FIGS. 6 A and B are line graphs that illustrate inhibition of platelet aggregation by $\alpha_{IIb}\beta_3$-specific and $\beta_3$-specific AgRP peptides. (A) Representative plot showing decrease in $A_{365}$ after platelet activation by 25 μM ADP in the presence or absence of varying concentrations of AgRP peptide 2bA. Concentrations are given in nM where indicated, while + and – represent activated and inactivated platelets, respectively. (B) Plot showing $A_{365}$ endpoints for different AgRP peptides and eptifibatide. Engineered AgRP peptide 7A, which binds to specifically to $\alpha_v\beta_3$ integrin, is included as a negative control.

Next, the effects of the engineered AgRP peptides on $\alpha_{IIb}\beta_3$-mediated platelet aggregation were studied. Three $\alpha_{IIb}\beta_3$-specific peptides (2bA, 2bJ, and 2bO) and two β3-specific peptides (b3A and b3I) were tested again. For comparison, a $\alpha_v\beta_3$-specific AgRP peptide (peptide 7A) from a prior study that binds $\alpha_v\beta_3$ integrin with a $K_D$ ~0.8 nM (19) and eptifibatide, an $\alpha_{IIb}\beta_3$-specific cyclic peptide (Mpr-Har-Gly-Asp-Trp-Pro-Cys (SEQ ID NO: 140), Mpr=mercaptopropionyl, Har=homoarginine), used clinically for inhibiting platelet aggregation, were also tested. Microtiter plates containing platelets in serum in the presence or absence of AgRP peptides were activated using ADP at a final concentration of 25 μM, and absorbance at 365 nm was monitored over 1 h. Coagulation of platelets triggered by ADP caused a decrease in the turbidity of the sample, which was quantified by measuring the absorbance at 365 nm, whereas for unactivated platelets sample turbidity was unchanged (or increased marginally). The engineered AgRP peptides inhibited platelet aggregation in dose-dependent manner (FIG. 6), with $IC_{50}$ values ranging from 50-110 nM (Table 5). The $IC_{50}$ values are similar and roughly correlate with the binding affinities measured against cell surface expressed $\alpha_{IIb}\beta_3$ integrin (Table 5). As expected, AgRP peptide 7A, which is highly specific for $\alpha_v\beta_3$ over other integrins, did not inhibit platelet aggregation, even at the highest concentrations, and seemed to slightly increase platelet aggregation. Eptifibatide treated resulted in an $IC_{50}$ of 80 nM, indicating that the engineered AgRP peptides are roughly as effective, or slightly more effective in the case of b3A and b3I, at inhibiting platelet aggregations. It should be noted that although b3A and b3I bind $\alpha_v\beta_3$ in addition to $\alpha_{IIb}\beta_3$, we attribute their slightly enhanced inhibitory ability to their increased relative affinity for $\alpha_{IIb}\beta_3$ integrin. It has been previously shown that there is no benefit to inhibiting platelet aggregation by co-targeting both $\beta_3$ integrins versus targeting $\alpha_{IIb}\beta_3$ alone.

TABLE 5

Summary of binding and platelet aggregation inhibition data for engineered AgRP peptides.

| | binding ($K_D$; nM) | | aggregation ($IC_{50}$; nM) |
|---|---|---|---|
| Clone | K562-$\alpha_{IIb}\beta_3$ | K562-$\alpha_v\beta_3$ | human platelets |
| b3A | 42 ± 3 | 23 ± 10 | 50 ± 3 |
| b3I | 70 ± 6 | 28 ± 14 | 66 ± 15 |
| 2bA | 87 ± 11 | nd[1] | 72 ± 8 |
| 2bJ | 59 ± 10 | nd[1] | 91 ± 18 |
| 2bO | 87 ± 17 | nd[1] | 110 ± 20 |
| eptifibatide | nd[2] | nd[2] | 94 ± 14 |

[1]Could not be determined because no binding was observed at the highest concentration tested, 1 μM.
[2]Not tested

Example 6

Engineered Agatoxin Peptides

It can be seen below that the wild-type knottin proteins AgRP and AgTX-1 and ATx2 share sequence homology:

```
                                   (SEQ ID NO: 3)
GCVRLHESCLGQQVPCCDPAATCYCRFFNAFCYCR
-AgRP

                                 (SEQ ID NO: 125)
GCIAEDYGKCTWGGTKCCRGRPCRCSMIGTNCECT
-AgTX-1 (1AGG, 1OMA, 1OMB)

                                 (SEQ ID NO: 126)
GCIAKDYGRCKWGGTPCCRGRGCICSIMGTNCECK
-AgTx2 (1OAV)
```

A Clustal W alignment of the above three sequences shows significant diversity at the amino acid level, but conserved cystine spacing, and three dimensional topology. The consensus sequence is GCIA-DYG-C-WGGTPCCRGR_C_CS_GTNCEC (SEQ ID NO: 141). BLAST 2 similarity score between AgtX-1 and AGtx2 is 77%; the BLAST 2 similarity score between agtX-1 and agrp is 34%.

Two constructs based on the closely related AgTx sequences shown above were prepared:

```
                                 (SEQ ID NO: 127)
GCIAEDYGRCTWGGTPCCRGRPCRCSMIGTNCECT
-AgTx consensus 1

                                 (SEQ ID NO: 128)
GCIAEDYGRCTWGGTPCCRGRGCICSIMGTNCECT
-AgTx consensus 2
```

Loop 4 from one of our engineered AgRP-based high affinity $\alpha_v\beta_3$ integrin binders (Silverman, J. Mol. Biol. 2009) is shown below.

```
                                   (SEQ ID NO: 129)
GCVRLHESCLGQQVPCCDPAATCYCSGRGDNDLVCYCR
AgRP 7A
```

This loop 4 was grafted into AgTx 1 and AgTx 2 consensus sequences to yield the following:

```
                                        (SEQ ID NO: 130)
GCIAEDYGRCTWGGTPCCRGRPCRCSGRGDNDLVCECT
AgTX-1-7A

                                        (SEQ ID NO: 131)
GCIAEDYGRCTWGGTPCCRGRGCICSGRGDNDLVCECT
AgTx2-7A
```

These AgTX-1-7A and AgTx2-7A sequences were cloned into the yeast display vector and tested for binding to $\alpha_v\beta_3$ integrin. Binding was observed at 10 nM $\alpha_v\beta_3$, the lowest concentration tested, indicating that these have high affinity for $\alpha_v\beta_3$ integrin and that swapping loops from AgRP to AgTx is a viable strategy.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A knottin peptide binding with high affinity to alpha IIb beta 3 integrin, having a sequence at least 90% identical to the sequence selected from the group consisting of:

(SEQ ID NO: 1)
GCVRLHESCLGQQVPCCDPAATCYC$X_1X_2$RGD$X_6X_7X_8X_9$ CYCR
and (SEQ ID NO: 2)
GCIAEDYGRCTWGGTPCCRGRGCIC$X_1X_2$RGD$X_6X_7X_8X_9$ CECT, where X residues are contained in a loop region and $X_1$ is K, L, R, V, Y or N;

$X_2$ is K or G;

$X_6$ is W, V, M or R;

$X_7$ is R, K or N;

$X_8$ is G, E, S, V, R, M, L, Q, or T; and $X_9$ is K, R, M or T.

2. The knottin peptide of claim 1, having essentially no binding to alpha v beta 3 integrin.

3. The knottin peptide of claim 2 wherein $X_6$ is W and $X_7$ and $X_9$ are each independently R or K.

4. The knottin peptide of claim 1, binding to both alpha IIb beta 3 integrin and alpha v beta 3 integrin, wherein said loop region comprises sequence:

$X_1$GRGDV$X_7$V$X_9$, (SEQ ID NO: 134)

wherein $X_7$ and $X_9$ are each independently R or K.

5. The knottin peptide of claim 1 having a sequence at least 95% identical to SEQ ID NO: 1, with the proviso that $X_1X_2$RGD$X_6X_7X_8X_9$ is selected from the group consisting of VGRGDVRRK (SEQ ID NO: 107); RGRGDVKLR, (SEQ ID NO: 112); LKRGDWKGK, (SEQ ID NO: 100); NKRGDWRSK, (SEQ ID NO: 105); and KKRGDWKER (SEQ ID NO: 106).

6. The knottin peptide of claim 1, wherein the peptide is SEQ ID NO: 1.

7. The knottin peptide of claim 1, wherein the peptide is SEQ ID NO: 2.

8. The peptide according to claim 1, further comprised in a composition comprising a pharmaceutically-acceptable carrier.

9. The peptide according to claim 2, further comprised in a composition comprising a pharmaceutically-acceptable carrier.

10. A knottin peptide having a scaffold at least 90% sequence identical to the agouti peptide according to SEQ ID NO: 1, GCVRLHESCLGQQVPCCDPAATCYC $X_1X_2$RGD$X_6X_7X_8X_9$CYCR, with the proviso that $X_1$ is K, L, R, V, Y or N;

$X_2$ is K or G;

$X_6$ is W, V, M or R;

$X_7$ is R, K or N;

$X_8$ is G, E, S, V, R, M, L, Q, or T; and $X_9$ is K, R, M or T.

11. A knottin peptide having a scaffold at least 90% identical to the agatoxin sequence GCIAEDYGRCTWGGTPCCRGRGCIC$X_1X_2$RGD$X_6$ $X_7X_8X_9$CECT (SEQ ID NO: 2), with the proviso that $X_1$ is K, L, R, V, Y or N;

$X_2$ is K or G;

$X_6$ is W, V, M or R;

$X_7$ is R, K or N;

$X_8$ is G, E, S, V, R, M, L, Q, or T; and $X_9$ is K, R, M or T.

12. A method of inhibiting platelet aggregation in a mammal which comprises administering an effective amount of a peptide having a sequence at least 90% identical to the sequence selected from the group consisting of: GCVRLHESCLGQQVPCCDPAATCYC$X_1X_2$RGD$X_6$ $X_7X_8X_9$CYCR (SEQ ID NO: 1) and GCIAEDYGRCTWGGTPCCRGRGCIC$X_1X_2$RGD$X_6$ $X_7X_8X_9$CECT (SEQ ID NO: 2), with the proviso that $X_1$ is K, L, R, V, Y or N;

$X_2$ is K or G;

$X_6$ is W, V, M or R;

$X_7$ is R, K or N;

$X_8$ is G, E, S, V, R, M, L, Q, or T; and $X_9$ is K, R, M or T.

13. The method of claim 12, wherein the peptide is contained in a pharmaceutical composition.

14. The method of claim 12, wherein the mammal is a human.

15. A method for preparing a peptide specifically binding to an alpha IIb beta 3 integrin, and not binding to a non-alpha IIb beta 3 integrin, comprising the steps of:

(a) preparing a library expressing a collection of peptides with different binding properties;

(b) selecting from said collection peptides that bind to alpha IIb beta 3 integrin to obtain a positive pool; and (c) selecting and removing from said positive pool peptides that bind to said non-alpha IIB beta-3 integrin.

16. The method of claim 15 wherein said peptides are expressed in recombinant yeast.

17. The method of claim 15 wherein said selecting step (b) is repeated to select peptides with higher binding affinity for alpha IIb beta 3 integrin.

18. A peptide binding specifically to alpha IIb beta 3 integrin, having a sequence at least 95% identical to the sequence GCVRLHESCLGQQVPCCDPAATCYC$X_1$K RGDW$X_7X_8X_9$CYCR (SEQ ID NO: 142), where $X_1$ is L, R, K, or N;

$X_7$ is K or R;

$X_8$ is G, V, S, or E; and $X_9$ is K, R, or M.

19. The peptide according to claim 18 comprising SEQ ID NO: 100.

20. A method of inhibiting platelet aggregation comprising contacting platelets with a peptide according to a sequence at least 95% identical to the sequence GCVRLHESCLGQQVPCCDPAATCYC$X_1$KRGDW $X_7X_8X_9$CYCR (SEQ ID NO: 142), where $X_1$ is L, R, K, or N;

$X_7$ is K or R;

$X_8$ is G, V, S, or E; and $X_9$ is K, R, or M.

* * * * *

SEQUENCE LISTING

```
<160> NUMBER OF SEQ ID NOS: 144

<210> SEQ ID NO 1
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys, Leu, Arg, Val, Tyr, or Asn
<220> FEATURE:
<221> NAME/KEY: MOD_RES
<222> LOCATION: (27)..(27)
<223> OTHER INFORMATION: Lys or Gly
<220> FEATURE:
<221> NAME/KEY: MOD_RES
<222> LOCATION: (31)..(31)
<223> OTHER INFORMATION: Trp, Val, Met, or Arg
<220> FEATURE:
<221> NAME/KEY: MOD_RES
<222> LOCATION: (32)..(32)
<223> OTHER INFORMATION: Arg, Lys, or Asn
<220> FEATURE:
<221> NAME/KEY: MOD_RES
<222> LOCATION: (33)..(33)
<223> OTHER INFORMATION: Gly, Glu, Ser, Val, Arg, Met, Leu, Gln, or Thr
<220> FEATURE:
<221> NAME/KEY: MOD_RES
<222> LOCATION: (34)..(34)
<223> OTHER INFORMATION: Lys, Arg, Met, or Thr

<400> SEQUENCE: 1

Gly Cys Val Arg Leu His Glu Ser Cys Leu Gly Gln Gln Val Pro Cys
1               5                   10                  15

Cys Asp Pro Ala Ala Thr Cys Tyr Cys Xaa Xaa Arg Gly Asp Xaa Xaa
            20                  25                  30

Xaa Xaa Cys Tyr Cys Arg
        35


<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys, Leu, Arg, Val, Tyr, or Asn
```

```
<220> FEATURE:
<221> NAME/KEY: MOD_RES
<222> LOCATION: (27)..(27)
<223> OTHER INFORMATION: Lys or Gly
<220> FEATURE:
<221> NAME/KEY: MOD_RES
<222> LOCATION: (31)..(31)
<223> OTHER INFORMATION: Trp, Val, Met, or Arg
<220> FEATURE:
<221> NAME/KEY: MOD_RES
<222> LOCATION: (32)..(32)
<223> OTHER INFORMATION: Arg, Lys, or Asn
<220> FEATURE:
<221> NAME/KEY: MOD_RES
<222> LOCATION: (33)..(33)
<223> OTHER INFORMATION: Gly, Glu, Ser, Val, Arg, Met, Leu, Gln, or Thr
<220> FEATURE:
<221> NAME/KEY: MOD_RES
<222> LOCATION: (34)..(34)
<223> OTHER INFORMATION: Lys, Arg, Met, or Thr

<400> SEQUENCE: 2

Gly Cys Ile Ala Glu Asp Tyr Gly Arg Cys Thr Trp Gly Gly Thr Pro
1               5                   10                  15

Cys Cys Arg Gly Arg Gly Cys Ile Cys Xaa Xaa Arg Gly Asp Xaa Xaa
            20                  25                  30

Xaa Xaa Cys Glu Cys Thr
        35


<210> SEQ ID NO 3
<211> LENGTH: 35
<212> TYPE: PRT
<213> ORGANISM: Homo sapiens

<400> SEQUENCE: 3

Gly Cys Val Arg Leu His Glu Ser Cys Leu Gly Gln Gln Val Pro Cys
1               5                   10                  15

Cys Asp Pro Ala Ala Thr Cys Tyr Cys Arg Phe Phe Asn Ala Phe Cys
            20                  25                  30

Tyr Cys Arg
        35


<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Arg or Lys

<400> SEQUENCE: 4

Xaa Lys Arg Gly Asp Trp Xaa Xaa Xaa
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Arg or Lys

<400> SEQUENCE: 5

Xaa Gly Arg Gly Asp Val Xaa Xaa Xaa
1               5


<210> SEQ ID NO 6
<211> LENGTH: 46
<212> TYPE: PRT
<213> ORGANISM: Homo sapiens

<400> SEQUENCE: 6

Cys Val Arg Leu His Glu Ser Cys Leu Gly Gln Gln Val Pro Cys Cys
1               5                   10                  15

Asp Pro Cys Ala Thr Cys Tyr Cys Arg Phe Phe Asn Ala Phe Cys Tyr
            20                  25                  30

Cys Arg Lys Leu Gly Thr Ala Met Asn Pro Cys Ser Arg Thr
        35                  40                  45


<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Val Arg
            20                  25                  30

Arg Lys Cys Tyr Cys Arg
        35


<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Cys Val Arg Leu His Glu Ser Cys Leu Gly Gln Gln Val Pro Cys
```

-continued

```
1               5                   10                  15

Cys Asp Pro Ala Ala Thr Cys Tyr Cys Val Gly Arg Gly Asp Met Asp
            20                  25                  30

Arg Arg Cys Tyr Cys Arg
        35


<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Val Lys
            20                  25                  30

Arg Glu Cys Tyr Cys Arg
        35


<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Val Asn
            20                  25                  30

Val Lys Cys Tyr Cys Arg
        35


<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Asn
            20                  25                  30

Arg Lys Cys Tyr Cys Arg
        35


<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Val Lys
            20                  25                  30

Met Arg Cys Tyr Cys Arg
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Thr Lys
            20                  25                  30

Met Lys Cys Tyr Cys Arg
        35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Val Arg
            20                  25                  30

Met Arg Cys Tyr Cys Arg
        35

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Val Arg
            20                  25                  30

Met Arg Cys Tyr Cys Arg
        35

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gly Cys Val Arg Leu His Glu Ser Cys Leu Gly Gln Gln Val Pro Cys
1               5                   10                  15

Cys Asp Pro Ala Ala Thr Cys Tyr Cys Met Gly Arg Gly Asp Val Lys
            20                  25                  30

Leu Arg Cys Tyr Cys Arg
        35


<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Cys Val Arg Leu His Glu Ser Cys Leu Gly Gln Gln Val Pro Cys
1               5                   10                  15

Cys Asp Pro Ala Ala Thr Cys Tyr Cys Met Gly Arg Gly Asp Thr Asp
            20                  25                  30

Met Lys Cys Tyr Cys Arg
        35


<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Cys Val Arg Leu His Glu Ser Cys Leu Gly Gln Gln Val Pro Cys
1               5                   10                  15

Cys Asp Pro Ala Ala Thr Cys Tyr Cys Lys Ser Arg Gly Asp Val Lys
            20                  25                  30

Val Lys Cys Tyr Cys Arg
        35


<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Val Lys
            20                  25                  30

Met Lys Cys Tyr Cys Arg
        35


<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 20

Gly Cys Val Arg Leu His Glu Ser Cys Leu Gly Gln Gln Val Pro Cys
1 5 10 15

Cys Asp Pro Ala Ala Thr Cys Tyr Cys Val Gly Arg Gly Asp Val Lys
20 25 30

Arg Lys Cys Tyr Cys Arg
35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Gly Cys Val Arg Leu His Glu Ser Cys Leu Gly Gln Gln Val Pro Cys
1 5 10 15

Cys Asp Pro Ala Ala Thr Cys Tyr Cys Val Gly Arg Gly Asp Met Arg
20 25 30

Arg Lys Cys Tyr Cys Arg
35

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Gly Cys Val Arg Leu His Glu Ser Cys Leu Gly Gln Gln Val Pro Cys
1 5 10 15

Cys Asp Pro Ala Ala Thr Cys Tyr Cys Leu Gly Arg Gly Asp Val Lys
20 25 30

Arg Arg Cys Tyr Cys Arg
35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Gly Cys Val Arg Leu His Glu Ser Cys Leu Gly Gln Gln Val Pro Cys
1 5 10 15

Cys Asp Pro Ala Ala Thr Cys Tyr Cys Ser Gly Arg Gly Asp Val Arg
20 25 30

Met Arg Cys Tyr Cys Arg
35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Gly Cys Val Arg Leu His Glu Ser Cys Leu Gly Gln Gln Val Pro Cys
1 5 10 15

Cys Asp Pro Pro Ala Thr Cys Tyr Cys Tyr Gly Arg Gly Asp Val Lys
20 25 30

Met Arg Cys Tyr Cys Arg
35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Gly Cys Val Arg Leu His Glu Ser Cys Leu Gly Gln Gln Val Pro Cys
1 5 10 15

Cys Asp Pro Ala Ala Thr Cys Tyr Cys Tyr Gly Arg Gly Asp Val Lys
20 25 30

Met Arg Cys Tyr Cys Arg
35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Met Val Cys Tyr Cys Arg
35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Leu Lys Cys Tyr Cys Arg
35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Leu Arg Cys Tyr Cys Arg
35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Thr Lys
20 25 30

Met Lys Cys Tyr Cys Arg
35

<210> SEQ ID NO 30
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gly Cys Val Arg Leu His Glu Ser Cys Leu Gly Gln Gln Val Pro Cys
1 5 10 15

Cys Asp Pro Ala Ala Thr Cys Tyr Cys Val Gly Arg Gly Asp Val Arg
20 25 30

Arg Lys Cys Tyr Cys Arg
35

<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gly Cys Val Arg Leu Asx Glu Ser Cys Leu Gly Gln Gln Val Pro Cys
1 5 10 15

Cys Asp Pro Ala Ala Thr Cys Tyr Cys Arg Gly Arg Gly Asp Val Arg
20 25 30

Arg Lys Cys Tyr Cys Arg
35

<210> SEQ ID NO 32
<211> LENGTH: 38
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 32

```
Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Val Arg
            20                  25                  30

Met Lys Cys Tyr Cys Arg
        35
```

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Val Lys
            20                  25                  30

Met Arg Cys Tyr Cys Arg
        35
```

<210> SEQ ID NO 34
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Val Lys
            20                  25                  30

Met Arg Cys Tyr Cys Arg
        35
```

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Gly Cys Val Arg Leu His Glu Ser Cys Ile Gly Gln Gln Val Pro Cys
1               5                   10                  15

Cys Asp Pro Ala Ala Thr Cys Tyr Cys Arg Gly Arg Gly Asp Val Lys
            20                  25                  30

Leu Arg Cys Tyr Cys Arg
        35
```

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Val Arg Cys Tyr Cys Arg
35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Leu Lys Cys Tyr Cys Arg
35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Gly Cys Val Arg Leu His Glu Ser Cys Leu Gly Gln Gln Val Pro Cys
1 5 10 15

Cys Asp Pro Ala Ala Thr Cys Tyr Cys Arg Gly Arg Gly Asp Val Lys
20 25 30

Arg Ile Cys Tyr Cys Arg
35

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Gly Cys Val Arg Leu His Glu Ser Cys Leu Gly Gln Gln Val Pro Cys
1 5 10 15

Cys Asp Pro Thr Ala Thr Cys Tyr Cys Lys Gly Arg Gly Asp Met Arg
20 25 30

Arg Arg Cys Tyr Cys Arg
35

<210> SEQ ID NO 40
<211> LENGTH: 38
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 40

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Val Asn
            20                  25                  30

Thr Arg Cys Tyr Cys Arg
        35


<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Arg Lys
            20                  25                  30

Gln Arg Cys Tyr Cys Arg
        35


<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Asp Trp Arg
            20                  25                  30

Gly Met Cys Tyr Cys Arg
        35


<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Cys Val Arg Leu His Glu Ser Cys Leu Gly Gln Gln Val Pro Cys
1               5                   10                  15

Cys Asp Pro Ala Ala Thr Cys Tyr Cys Gly Lys Arg Gly Asp Trp Lys
            20                  25                  30

Gly Lys Cys Tyr Cys Arg
        35


<210> SEQ ID NO 44
<211> LENGTH: 38
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Gly Cys Val Arg Leu His Glu Ser Cys Leu Gly Gln Gln Val Pro Cys
1 5 10 15

Cys Asp Pro Ala Ala Thr Cys Tyr Cys Asn Lys Arg Gly Asp Trp Arg
20 25 30

Ser Lys Cys Tyr Cys Arg
35

<210> SEQ ID NO 45
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Gly Cys Val Arg Leu His Glu Ser Cys Leu Gly Gln Gln Val Pro Cys
1 5 10 15

Cys Asp Pro Ala Ala Thr Cys Tyr Cys Tyr Lys Arg Gly Asp Trp Lys
20 25 30

Ser Arg Cys Tyr Cys Arg
35

<210> SEQ ID NO 46
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Trp Arg
20 25 30

Glu Ala Cys Tyr Cys Arg
35

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Trp Arg
20 25 30

Glu Ala Cys Tyr Cys Arg
35

<210> SEQ ID NO 48

<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Trp Lys
20 25 30

Glu Glu Cys Tyr Cys Arg
35

<210> SEQ ID NO 49
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Gly Cys Val Arg Leu His Glu Ser Cys Leu Gly Gln Gln Val Pro Cys
1 5 10 15

Cys Asp Pro Ala Ala Thr Cys Tyr Cys Val Lys Arg Gly Asp Arg Lys
20 25 30

Glu Lys Cys Tyr Cys Arg
35

<210> SEQ ID NO 50
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Gly Cys Val Arg Leu His Glu Ser Cys Leu Gly Gln Gln Val Pro Cys
1 5 10 15

Cys Asp Pro Ala Ala Thr Cys Tyr Cys Val Lys Arg Gly Asp Arg Lys
20 25 30

Glu Lys Cys Tyr Cys Arg
35

<210> SEQ ID NO 51
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Arg Lys
20 25 30

Glu Glu Cys Tyr Cys Arg
35

```
<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Cys Val Arg Leu His Glu Ser Cys Leu Gly Gln Gln Val Pro Cys
1               5                   10                  15

Cys Asp Pro Ala Ala Thr Cys Tyr Cys Pro Lys Arg Gly Asp Glu Arg
            20                  25                  30

Val Arg Cys Tyr Cys Arg
        35


<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Cys Val Lys Leu His Glu Ser Cys Leu Gly Gln Gln Val Pro Cys
1               5                   10                  15

Cys Asp Pro Ala Ala Thr Cys Tyr Cys Pro Arg Arg Gly Asp Glu Lys
            20                  25                  30

His Lys Cys Tyr Cys Arg
        35


<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Cys Val Arg Leu His Glu Ser Cys Leu Gly Gln Gln Val Pro Cys
1               5                   10                  15

Cys Asp Pro Ala Ala Thr Cys Tyr Cys Leu Lys Arg Gly Asp Trp Lys
            20                  25                  30

Glu Lys Cys Tyr Cys Arg
        35


<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Cys Val Arg Leu His Glu Ser Cys Leu Gly Gln Gln Val Pro Cys
1               5                   10                  15

Cys Asp Pro Ala Ala Thr Cys Tyr Cys Asn Lys Arg Gly Asp Trp Lys
            20                  25                  30

Asp Lys Cys Tyr Cys Arg
        35
```

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Gly Asp Trp Arg
            20                  25                  30

Glu Ala Cys Tyr Cys Arg
        35
```

<210> SEQ ID NO 57
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gly Cys Val Arg Leu Arg Glu Ser Cys Leu Gly Gln Gln Val Pro Cys
1               5                   10                  15

Cys Asp Pro Ala Ala Thr Cys Tyr Cys Arg Lys Arg Gly Asp Trp Arg
            20                  25                  30

Gly Met Cys Tyr Cys Arg
        35
```

<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Asp Trp Arg
            20                  25                  30

Gly Met Cys Tyr Cys Arg
        35
```

<210> SEQ ID NO 59
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Asp Trp Arg
            20                  25                  30

Gly Met Cys Tyr Cys Arg
        35
```

```
<210> SEQ ID NO 60
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Cys Val Arg Val His Glu Ser Cys Leu Gly Gln Gln Val Pro Cys
1               5                   10                  15

Cys Asp Pro Ala Ala Thr Cys Tyr Cys Trp Ala Arg Cys Asp Trp Arg
            20                  25                  30

Glu Lys Cys Tyr Cys Arg
        35


<210> SEQ ID NO 61
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Cys Val Arg Leu His Glu Ser Cys Leu Gly Gln Gln Val Pro Cys
1               5                   10                  15

Cys Asp Pro Ala Ala Thr Cys Tyr Cys Arg Leu Arg Gly Asp Val Lys
            20                  25                  30

Trp Leu Cys Tyr Cys Arg
        35


<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Cys Val Arg Leu His Glu Ser Cys Leu Gly Gln Gln Val Pro Cys
1               5                   10                  15

Cys Asp Pro Ala Ala Thr Cys Tyr Cys Arg Arg Arg Gly Asp Glu Lys
            20                  25                  30

Trp Gly Cys Tyr Cys Arg
        35


<210> SEQ ID NO 63
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Cys Val Arg Leu His Glu Ser Cys Leu Gly Gln Gln Val Pro Cys
1               5                   10                  15

Cys Asp Pro Ala Ala Thr Cys Tyr Cys Lys Thr Arg Gly Asp Arg Lys
            20                  25                  30

Met Arg Cys Tyr Cys Arg
```

35

<210> SEQ ID NO 64
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Gly Cys Val Arg Leu His Glu Ser Cys Leu Gly Gln Gln Val Pro Cys
1 5 10 15

Cys Asp Pro Ala Ala Thr Cys Tyr Cys Lys Arg Arg Glx Asp Val Lys
20 25 30

Met Thr Cys Tyr Cys Arg
35

<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Gly Cys Val Arg Leu His Glu Ser Cys Leu Gly Gln Gln Val Pro Cys
1 5 10 15

Cys Asp Pro Ala Ala Thr Cys Tyr Cys Pro Lys Arg Gly Asp Arg Lys
20 25 30

Val Trp Cys Tyr Cys Arg
35

<210> SEQ ID NO 66
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Gly Cys Val Arg Leu His Glu Ser Cys Leu Gly Gln Gln Val Pro Cys
1 5 10 15

Cys Asp Pro Ala Ala Thr Cys Tyr Cys Asn Val Lys Gly Asp Trp Gly
20 25 30

Glu Arg Cys Tyr Cys Arg
35

<210> SEQ ID NO 67
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gly Cys Val Lys Leu His Glu Ser Cys Leu Gly Gln Gln Val Pro Cys
1 5 10 15

Cys Asp Pro Ala Ala Thr Cys Tyr Cys Gly Lys Arg Gly Asp Trp Arg
20 25 30

```
Gly Arg Cys Tyr Cys Arg
        35


<210> SEQ ID NO 68
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Cys Asp Trp Lys
            20                  25                  30

Gly His Cys Tyr Cys Arg
        35


<210> SEQ ID NO 69
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Cys Val Arg Leu His Glu Ser Cys Leu Gly Gln Gln Val Pro Cys
1               5                   10                  15

Cys Asp Pro Ala Ala Thr Cys Tyr Cys Leu Lys Arg Gly Asp Trp Lys
            20                  25                  30

Glu Lys Cys Tyr Cys Arg
        35


<210> SEQ ID NO 70
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Cys Val Arg Leu His Glu Ser Cys Leu Gly Gln Gln Val Pro Cys
1               5                   10                  15

Cys Asp Pro Ala Ala Thr Cys Tyr Cys Leu Lys Lys Gly Asp Trp Lys
            20                  25                  30

Gly Lys Cys Tyr Cys Arg
        35


<210> SEQ ID NO 71
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Cys Val Arg Leu His Glu Ser Cys Leu Gly Gln Gln Val Pro Cys
1               5                   10                  15

Cys Asp Pro Ala Ala Thr Cys Tyr Cys Asn Lys Arg Gly Asp Trp Lys
            20                  25                  30
```

```
Asp Lys Cys Tyr Cys Arg
        35


<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Cys Val Arg Leu His Glu Ser Cys Leu Gly Gln Gln Val Pro Cys
1               5                   10                  15

Cys Asp Pro Ala Ala Thr Cys Tyr Cys Ile Lys Arg Gly Asp Trp Arg
            20                  25                  30

Gly Val Cys Tyr Cys Arg
        35


<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Cys Asp Val Lys
            20                  25                  30

Trp Asp Cys Tyr Cys Arg
        35


<210> SEQ ID NO 74
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Cys Val Arg Leu His Glu Ser Cys Leu Gly Gln Gln Val Pro Cys
1               5                   10                  15

Cys Asp Pro Ala Ala Thr Cys Tyr Cys Lys Arg Arg Gly Asp Leu Asp
            20                  25                  30

Trp Leu Cys Tyr Cys Arg
        35


<210> SEQ ID NO 75
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Cys Val Arg Leu His Glu Ser Cys Leu Gly Gln Gln Val Pro Cys
1               5                   10                  15

Cys Asp Pro Ala Ala Thr Cys Tyr Cys Arg Arg Arg Gly Asp Leu Lys
```

20 25 30

Pro Leu Cys Tyr Cys Arg
35

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Gly Cys Val Arg Leu His Glu Ser Cys Leu Gly Gln Gln Val Pro Cys
1 5 10 15

Cys Asp Pro Ala Ala Thr Cys Tyr Cys Lys Cys Lys Gly Asp Arg Arg
20 25 30

Cys Lys Cys Tyr Cys Arg
35

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Gly Cys Val Arg Leu His Glu Ser Cys Leu Gly Gln Gln Val Pro Cys
1 5 10 15

Cys Asp Pro Ala Ala Thr Cys Tyr Cys Met Lys Arg Gly Asp Trp Arg
20 25 30

Gly Val Cys Tyr Cys Arg
35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Gly Cys Val Arg Leu His Glu Ser Cys Leu Gly Gln Gln Val Pro Cys
1 5 10 15

Cys Asp Pro Ala Ala Thr Cys Tyr Cys Leu Lys Arg Gly Asp Trp Arg
20 25 30

Gly Lys Cys Tyr Cys Arg
35

<210> SEQ ID NO 79
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Gly Cys Val Arg Leu Arg Glu Ser Cys Leu Gly Gln Gln Val Pro Cys
1 5 10 15

Cys Asp Pro Ala Ala Thr Cys Tyr Cys Leu Lys Arg Gly Asp Trp Lys
20 25 30

Gly Lys Cys Tyr Cys Arg
35

<210> SEQ ID NO 80
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

Gly Cys Val Arg Leu His Glu Ser Cys Leu Gly Gln Gln Val Pro Cys
1 5 10 15

Cys Asp Pro Ala Ala Thr Cys Tyr Cys Arg Lys Arg Gly Asp Trp Arg
20 25 30

Gly Met Cys Tyr Cys Arg
35

<210> SEQ ID NO 81
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Trp Arg
20 25 30

Gly Arg Cys Tyr Cys Arg
35

<210> SEQ ID NO 82
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Gly Cys Val Arg Leu His Glu Ser Cys Leu Gly Gln Gln Val Pro Cys
1 5 10 15

Cys Asp Pro Ala Ala Thr Cys Tyr Cys Lys Lys Arg Gly Asp Trp Arg
20 25 30

Ser Lys Cys Tyr Cys Arg
35

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Gly Cys Val Arg Leu His Glu Ser Cys Leu Gly Gln Gln Val Pro Cys
1 5 10 15

```
Cys Asp Pro Ala Ala Thr Cys Tyr Cys Arg Lys Arg Gly Glu Trp Lys
            20                  25                  30

Asp Glu Cys Tyr Cys Arg
        35


<210> SEQ ID NO 84
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Cys Trp Lys
            20                  25                  30

Met Val Cys Tyr Cys Arg
        35


<210> SEQ ID NO 85
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Asp Trp Lys
            20                  25                  30

Ala Thr Cys Tyr Cys Arg
        35


<210> SEQ ID NO 86
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Gly Asp Trp Arg
            20                  25                  30

Val Thr Cys Tyr Cys Arg
        35


<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Cys Val Arg Leu His Glu Ser Cys Leu Gly Gln Gln Val Pro Cys
```

-continued

```
1               5                   10                  15

Cys Asp Pro Ala Ala Thr Cys Tyr Cys Arg Lys Arg Gly Asp Val Arg
            20                  25                  30

Ser Arg Cys Tyr Cys Arg
        35


<210> SEQ ID NO 88
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Cys Val Arg Leu His Glu Ser Cys Leu Gly Gln Gln Val Pro Cys
1               5                   10                  15

Cys Asp Pro Ala Ala Thr Cys Tyr Cys Arg Arg Arg Gly Cys Val Lys
            20                  25                  30

Asn Lys Cys Tyr Cys Arg
        35


<210> SEQ ID NO 89
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Cys Val Arg Leu His Glu Ser Cys Leu Gly Gln Gln Val Pro Cys
1               5                   10                  15

Cys Asp Pro Ala Ala Thr Cys Tyr Cys Leu Lys Arg Gly Asp Trp Lys
            20                  25                  30

Gly Lys Cys Tyr Cys Arg
        35


<210> SEQ ID NO 90
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Cys Val Arg Leu His Glu Ser Cys Leu Gly Gln Gln Val Pro Cys
1               5                   10                  15

Cys Asp Pro Ala Ala Thr Cys Tyr Cys Leu Lys Arg Gly Asp Trp Arg
            20                  25                  30

Gly Arg Cys Tyr Cys Arg
        35


<210> SEQ ID NO 91
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91
```

-continued

```
Gly Cys Val Arg Leu His Glu Ser Cys Leu Gly Gln Gln Val Pro Cys
1               5                   10                  15

Cys Asp Pro Ala Ala Thr Cys Tyr Cys Arg Lys Arg Gly Asp Trp Arg
            20                  25                  30

Gly Met Cys Tyr Cys Arg
        35


<210> SEQ ID NO 92
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Gly Asp Trp Arg
            20                  25                  30

Gly Arg Cys Tyr Cys Arg
        35


<210> SEQ ID NO 93
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Gly Asp Trp Arg
            20                  25                  30

Val Lys Cys Tyr Cys Arg
        35


<210> SEQ ID NO 94
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Cys Val Arg Leu His Glu Ser Cys Leu Gly Gln Gln Val Pro Cys
1               5                   10                  15

Cys Asp Pro Ala Ala Thr Cys Tyr Cys Asn Lys Arg Gly Asp Trp Arg
            20                  25                  30

Ser Lys Cys Tyr Cys Arg
        35


<210> SEQ ID NO 95
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

```
Gly Cys Val Arg Leu His Glu Ser Cys Leu Gly Gln Gln Val Pro Cys
1               5                   10                  15

Cys Asp Pro Ala Ala Thr Cys Tyr Cys Lys Lys Arg Gly Asp Trp Lys
            20                  25                  30

Glu Arg Cys Tyr Cys Arg
        35


<210> SEQ ID NO 96
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
            20                  25                  30

Asn Cys Glu Cys Thr Pro Arg Leu Ile Met Glu Gly Leu Ser Phe Ala
        35                  40                  45


<210> SEQ ID NO 97
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Lys Lys Lys Cys Ile Ala Lys Asp Tyr Gly Arg Cys Lys Trp Gly Gly
1               5                   10                  15

Thr Pro Cys Cys Arg Gly Arg Gly Cys Ile Cys Ser Ile Met Gly Thr
            20                  25                  30

Asn Cys Glu Cys Lys Pro Arg Leu Ile Met Glu Gly Leu Gly Leu Ala
        35                  40                  45


<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Gly Arg Gly Asp Ser Pro Ala Ser
1               5


<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Gln Lys Leu Ile Ser Glu Glu Asp Leu
1               5                   10
```

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Leu Lys Arg Gly Asp Trp Lys Gly Lys
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Leu Lys Arg Gly Asp Trp Arg Gly Arg
1 5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Arg Lys Arg Gly Asp Trp Arg Gly Met
1 5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Lys Lys Arg Gly Asp Trp Arg Gly Arg
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Lys Lys Arg Gly Asp Trp Arg Val Lys
1 5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Asn Lys Arg Gly Asp Trp Arg Ser Lys
1 5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Lys Lys Arg Gly Asp Trp Lys Glu Arg
1 5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Val Gly Arg Gly Asp Val Arg Arg Lys
1 5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Gly Arg Gly Asp Val Arg Arg Lys
1 5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Lys Gly Arg Gly Asp Val Arg Met Lys
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Tyr Gly Arg Gly Asp Val Lys Met Arg
1 5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Arg Gly Arg Gly Asp Val Lys Met Arg
1 5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Arg Gly Arg Gly Asp Val Lys Leu Arg
1 5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Arg Gly Arg Gly Asp Val Lys Val Arg
1 5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Arg Gly Arg Gly Asp Val Lys Leu Lys
1 5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Arg Gly Arg Gly Asp Val Lys Arg Ile
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Lys Gly Arg Gly Asp Met Arg Arg Arg
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Val Gly Arg Gly Asp Val Asn Thr Arg
1 5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Ile Gly Arg Gly Asp Arg Lys Gln Arg
1 5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Ser Gly Arg Gly Asp Asn Asp Leu Val
1 5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Lys Gly Arg Gly Asp Ala Arg Leu Gln
1 5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Tyr Gly Arg Gly Asp Asn Asp Leu Arg
1 5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Val Gly Arg Gly Asp Asp Asn Leu Lys
1 5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Glu Gly Arg Gly Asp Arg Asp Met Lys
1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Asp Tyr Lys Asp Asp Asp Asp Lys
1 5

<210> SEQ ID NO 125
<211> LENGTH: 35
<212> TYPE: PRT
<213> ORGANISM: Unknown
<220> FEATURE:
<223> OTHER INFORMATION: Description of Unknown: Agatoxin peptide

<400> SEQUENCE: 125

Gly Cys Ile Ala Glu Asp Tyr Gly Lys Cys Thr Trp Gly Gly Thr Lys
1 5 10 15

Cys Cys Arg Gly Arg Pro Cys Arg Cys Ser Met Ile Gly Thr Asn Cys
20 25 30

Glu Cys Thr
35

<210> SEQ ID NO 126
<211> LENGTH: 35
<212> TYPE: PRT
<213> ORGANISM: Unknown
<220> FEATURE:
<223> OTHER INFORMATION: Description of Unknown: Agatoxin peptide

<400> SEQUENCE: 126

Gly Cys Ile Ala Lys Asp Tyr Gly Arg Cys Lys Trp Gly Gly Thr Pro
1 5 10 15

Cys Cys Arg Gly Arg Gly Cys Ile Cys Ser Ile Met Gly Thr Asn Cys
20 25 30

Glu Cys Lys
35

<210> SEQ ID NO 127
<211> LENGTH: 35
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 127

Gly Cys Ile Ala Glu Asp Tyr Gly Arg Cys Thr Trp Gly Gly Thr Pro
1 5 10 15

Cys Cys Arg Gly Arg Pro Cys Arg Cys Ser Met Ile Gly Thr Asn Cys
20 25 30

Glu Cys Thr
35

<210> SEQ ID NO 128
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 128

Gly Cys Ile Ala Glu Asp Tyr Gly Arg Cys Thr Trp Gly Gly Thr Pro
1 5 10 15

Cys Cys Arg Gly Arg Gly Cys Ile Cys Ser Ile Met Gly Thr Asn Cys
20 25 30

Glu Cys Thr
35

<210> SEQ ID NO 129
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 129

Gly Cys Val Arg Leu His Glu Ser Cys Leu Gly Gln Gln Val Pro Cys
1 5 10 15

Cys Asp Pro Ala Ala Thr Cys Tyr Cys Ser Gly Arg Gly Asp Asn Asp
20 25 30

Leu Val Cys Tyr Cys Arg
35

<210> SEQ ID NO 130
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 130

Gly Cys Ile Ala Glu Asp Tyr Gly Arg Cys Thr Trp Gly Gly Thr Pro
1 5 10 15

Cys Cys Arg Gly Arg Pro Cys Arg Cys Ser Gly Arg Gly Asp Asn Asp
20 25 30

Leu Val Cys Glu Cys Thr
35

<210> SEQ ID NO 131
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 131

Gly Cys Ile Ala Glu Asp Tyr Gly Arg Cys Thr Trp Gly Gly Thr Pro
1 5 10 15

Cys Cys Arg Gly Arg Gly Cys Ile Cys Ser Gly Arg Gly Asp Asn Asp
20 25 30

Leu Val Cys Glu Cys Thr
35

<210> SEQ ID NO 132
<211> LENGTH: 47
<212> TYPE: PRT
<213> ORGANISM: Homo sapiens

<400> SEQUENCE: 132

Gly Cys Val Arg Leu His Glu Ser Cys Leu Gly Gln Gln Val Pro Cys
1 5 10 15

Cys Asp Pro Cys Ala Thr Cys Tyr Cys Arg Phe Phe Asn Ala Phe Cys
20 25 30

Tyr Cys Arg Lys Leu Gly Thr Ala Met Asn Pro Cys Ser Arg Thr
35 40 45

<210> SEQ ID NO 133
<211> LENGTH: 48
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 133

Glu Asp Asn Cys Ile Ala Glu Asp Tyr Gly Lys Cys Thr Trp Gly Gly
1 5 10 15

Thr Lys Cys Cys Arg Gly Arg Pro Cys Arg Cys Ser Met Ile Gly Thr
20 25 30

Asn Cys Glu Cys Thr Pro Arg Leu Ile Met Glu Gly Leu Ser Phe Ala
35 40 45

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Lys, Leu, Arg, Val, Tyr, or Asn
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (9)..(9)
<223> OTHER INFORMATION: Arg or Lys

<400> SEQUENCE: 134

Xaa Gly Arg Gly Asp Val Xaa Val Xaa
1 5

<210> SEQ ID NO 135
<211> LENGTH: 6
<212> TYPE: PRT
<213> ORGANISM: Homo sapiens

<400> SEQUENCE: 135

Arg Phe Phe Asn Ala Phe
1 5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 136

His His His His His His
1 5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Any amino acid

<400> SEQUENCE: 137

Arg Gly Asp Trp Xaa Glu
1 5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Gly Arg Gly Asp Val
1 5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Asn or Asp

<400> SEQUENCE: 139

Gly Arg Gly Asp Xaa
1 5

<210> SEQ ID NO 140
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mercaptopropionyl homoarginine
<220> FEATURE:
<221> NAME/KEY: misc_feature
<222> LOCATION: (1)..(6)
<223> OTHER INFORMATION: Cyclic peptide

<400> SEQUENCE: 140

Xaa Gly Asp Trp Pro Cys
1               5


<210> SEQ ID NO 141
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Leu, Glu, or Lys
<220> FEATURE:
<221> NAME/KEY: MOD_RES
<222> LOCATION: (9)..(9)
<223> OTHER INFORMATION: Cys, Lys, or Arg
<220> FEATURE:
<221> NAME/KEY: MOD_RES
<222> LOCATION: (11)..(11)
<223> OTHER INFORMATION: Gly, Thr, or Lys
<220> FEATURE:
<221> NAME/KEY: MOD_RES
<222> LOCATION: (22)..(22)
<223> OTHER INFORMATION: Thr, Pro, or Gly
<220> FEATURE:
<221> NAME/KEY: MOD_RES
<222> LOCATION: (24)..(24)
<223> OTHER INFORMATION: Tyr, Arg, or Ile
<220> FEATURE:
<221> NAME/KEY: MOD_RES
<222> LOCATION: (27)..(28)
<223> OTHER INFORMATION: Phe, Met, or Ile
<220> FEATURE:
<221> NAME/KEY: MOD_RES
<222> LOCATION: (35)..(35)
<223> OTHER INFORMATION: Arg, Thr, or Lys

<400> SEQUENCE: 141

Gly Cys Ile Ala Xaa Asp Tyr Gly Xaa Cys Xaa Trp Gly Gly Thr Pro
1               5                   10                  15

Cys Cys Arg Gly Arg Xaa Cys Xaa Cys Ser Xaa Xaa Gly Thr Asn Cys
            20                  25                  30

Glu Cys Xaa
        35


<210> SEQ ID NO 142
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Leu, Arg, Lys, or Asn
<220> FEATURE:
<221> NAME/KEY: MOD_RES
```

```
<222> LOCATION: (32)..(32)
<223> OTHER INFORMATION: Lys or Arg
<220> FEATURE:
<221> NAME/KEY: MOD_RES
<222> LOCATION: (33)..(33)
<223> OTHER INFORMATION: Gly, Val, Ser, or Glu
<220> FEATURE:
<221> NAME/KEY: MOD_RES
<222> LOCATION: (34)..(34)
<223> OTHER INFORMATION: Lys, Arg, or Met

<400> SEQUENCE: 142

Gly Cys Val Arg Leu His Glu Ser Cys Leu Gly Gln Gln Val Pro Cys
1               5                   10                  15

Cys Asp Pro Ala Ala Thr Cys Tyr Cys Xaa Lys Arg Gly Asp Trp Xaa
            20                  25                  30

Xaa Xaa Cys Tyr Cys Arg
        35


<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Leu, Asn, or Arg
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(8)
<223> OTHER INFORMATION: Gly, Glu, Ser, or Val
<220> FEATURE:
<221> NAME/KEY: MOD_RES
<222> LOCATION: (9)..(9)
<223> OTHER INFORMATION: Lys, Arg, or Met

<400> SEQUENCE: 143

Xaa Lys Arg Gly Asp Trp Xaa Xaa Xaa
1               5


<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Lys, Val, Ile, or Tyr
<220> FEATURE:
<221> NAME/KEY: MOD_RES
<222> LOCATION: (6)..(6)
<223> OTHER INFORMATION: Val, Met, or Arg
<220> FEATURE:
<221> NAME/KEY: MOD_RES
<222> LOCATION: (7)..(7)
<223> OTHER INFORMATION: Lys, Arg, or Asn
<220> FEATURE:
<221> NAME/KEY: MOD_RES
<222> LOCATION: (8)..(8)
<223> OTHER INFORMATION: Arg, Met, Leu, Gln, Thr, or Val
<220> FEATURE:
<221> NAME/KEY: MOD_RES
<222> LOCATION: (9)..(9)
```

-continued

```
<223> OTHER INFORMATION: Arg, Lys, or Ile

<400> SEQUENCE: 144

Xaa Gly Arg Gly Asp Xaa Xaa Xaa Xaa
1               5
```